(12) United States Patent
Pananen et al.

(10) Patent No.: US 10,086,133 B2
(45) Date of Patent: Oct. 2, 2018

(54) SYSTEMS FOR SET CONNECTOR ASSEMBLY WITH LOCK

(71) Applicant: MEDTRONIC MINIMED, INC., Northridge, CA (US)

(72) Inventors: Jacob E. Pananen, Santa Monica, CA (US); Mitchell T. Johnson, Burbank, CA (US); Ella Isabella F. Ella, Chino Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 105 days.

(21) Appl. No.: 15/166,049

(22) Filed: May 26, 2016

(65) Prior Publication Data

US 2017/0340816 A1  Nov. 30, 2017

(51) Int. Cl.
| | |
|---|---|
| *A61M 25/16* | (2006.01) |
| *A61M 25/18* | (2006.01) |
| *A61M 39/00* | (2006.01) |
| *A61M 39/10* | (2006.01) |
| *A61M 5/162* | (2006.01) |
| *A61M 39/12* | (2006.01) |
| *A61M 5/142* | (2006.01) |

(52) U.S. Cl.
CPC ........ *A61M 5/162* (2013.01); *A61M 5/14244* (2013.01); *A61M 39/10* (2013.01); *A61M 39/1011* (2013.01); *A61M 39/12* (2013.01)

(58) Field of Classification Search
CPC .............. A61M 5/162; A61M 5/14244; A61M 39/1011; A61M 39/12; A61M 2039/1072; A61M 2039/1016; A61M 39/10; A61M 25/0014; A61M 2039/1027; A61M 2039/1033; A61M 2039/1044; A61M 2039/1077
USPC ......................................................... 604/533
See application file for complete search history.

(56) References Cited

U.S. PATENT DOCUMENTS

| | | |
|---|---|---|
| 4,562,751 A | 1/1986 | Nason et al. |
| 4,678,408 A | 7/1987 | Nason et al. |
| 4,685,903 A | 8/1987 | Cable et al. |
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |

(Continued)

FOREIGN PATENT DOCUMENTS

| | | |
|---|---|---|
| EP | 0459812 A1 | 12/1991 |
| EP | 2298406 A1 | 3/2011 |

(Continued)

*Primary Examiner* — Jason Flick
(74) *Attorney, Agent, or Firm* — Lorenz & Kopf, LLP

(57) ABSTRACT

A set connector assembly for a fluid infusion device is provided. The set connector assembly includes a connector having a body. The body defines a graspable portion and a coupling portion, and the coupling portion is to be received within a portion of the fluid infusion device. The graspable portion has at least one locking tab to lock the connector to the fluid infusion device, and the graspable portion is movable relative to the body to move the connector between a first, locked position and a second, unlocked position relative to the fluid infusion device.

17 Claims, 14 Drawing Sheets

(56) References Cited

U.S. PATENT DOCUMENTS

| | | |
|---|---|---|
| 5,665,065 A | 9/1997 | Colman et al. |
| 5,688,254 A | 11/1997 | Lopez et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,905,868 B2 | 3/2011 | Moberg et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2006/0259013 A1 | 11/2006 | Ranalletta et al. |
| 2007/0123819 A1 | 5/2007 | Mernoe et al. |
| 2008/0269687 A1 | 10/2008 | Chong et al. |
| 2009/0299290 A1 | 12/2009 | Moberg |
| 2010/0160861 A1 | 6/2010 | Causey, III et al. |
| 2014/0088550 A1* | 3/2014 | Bene .................... A61M 5/158 604/506 |
| 2016/0049098 A1 | 2/2016 | Swanson et al. |
| 2016/0095987 A1 | 4/2016 | Chattaraj et al. |
| 2017/0027820 A1 | 2/2017 | Okiyama et al. |

FOREIGN PATENT DOCUMENTS

| | | |
|---|---|---|
| EP | 2439437 A1 | 4/2012 |
| EP | 2669564 A2 | 12/2013 |
| EP | 2837403 A1 | 2/2015 |
| WO | WO 97/36636 A1 | 10/1997 |

* cited by examiner

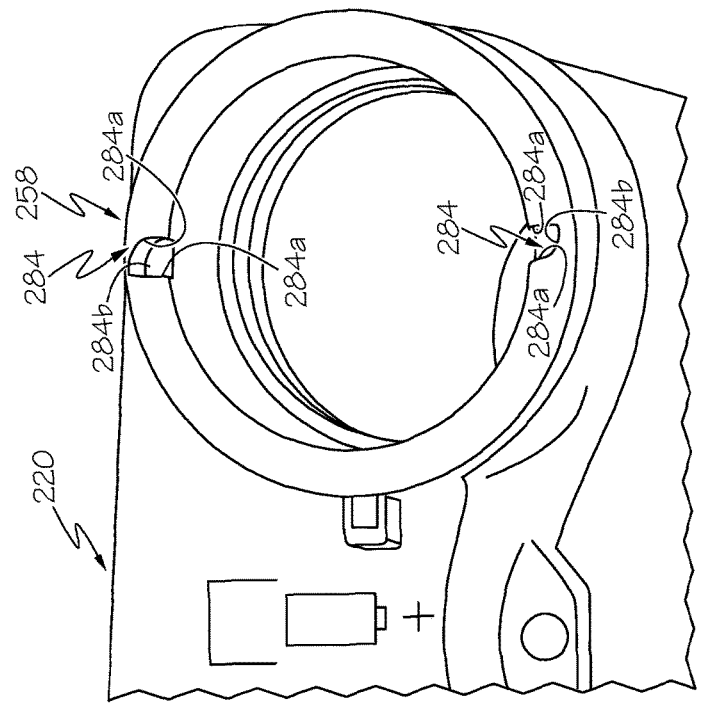
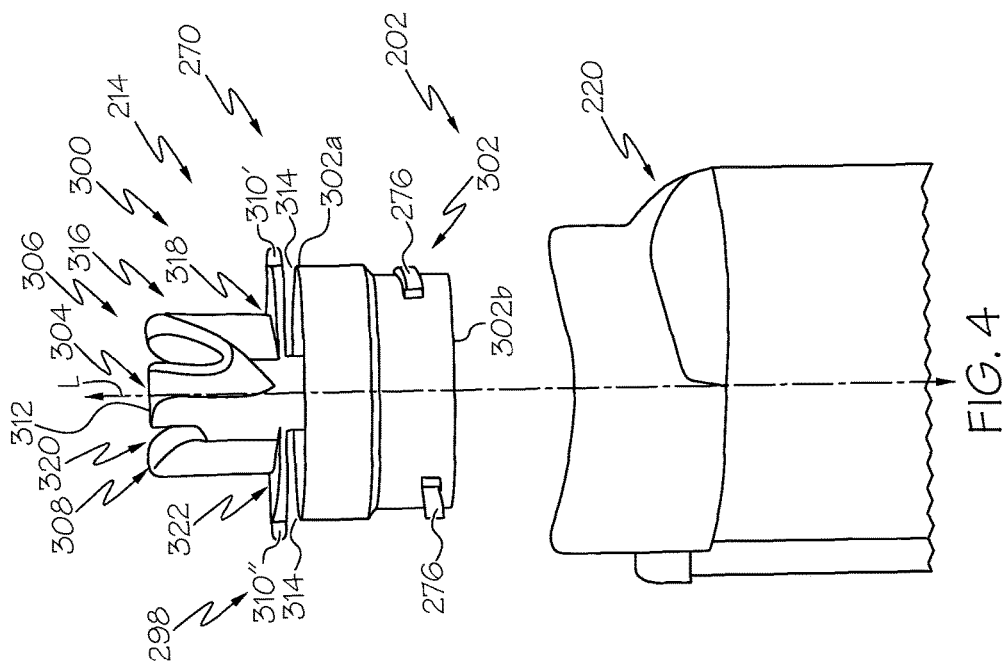

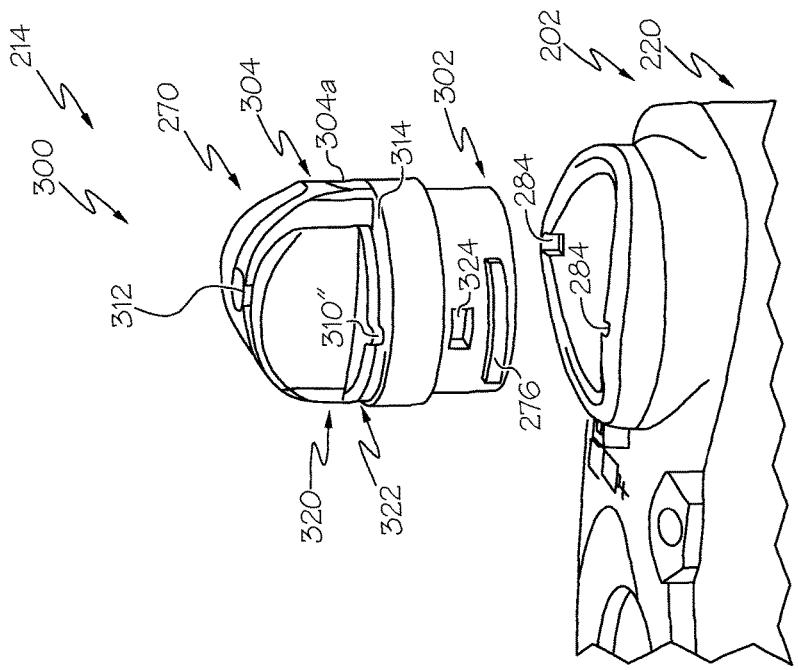
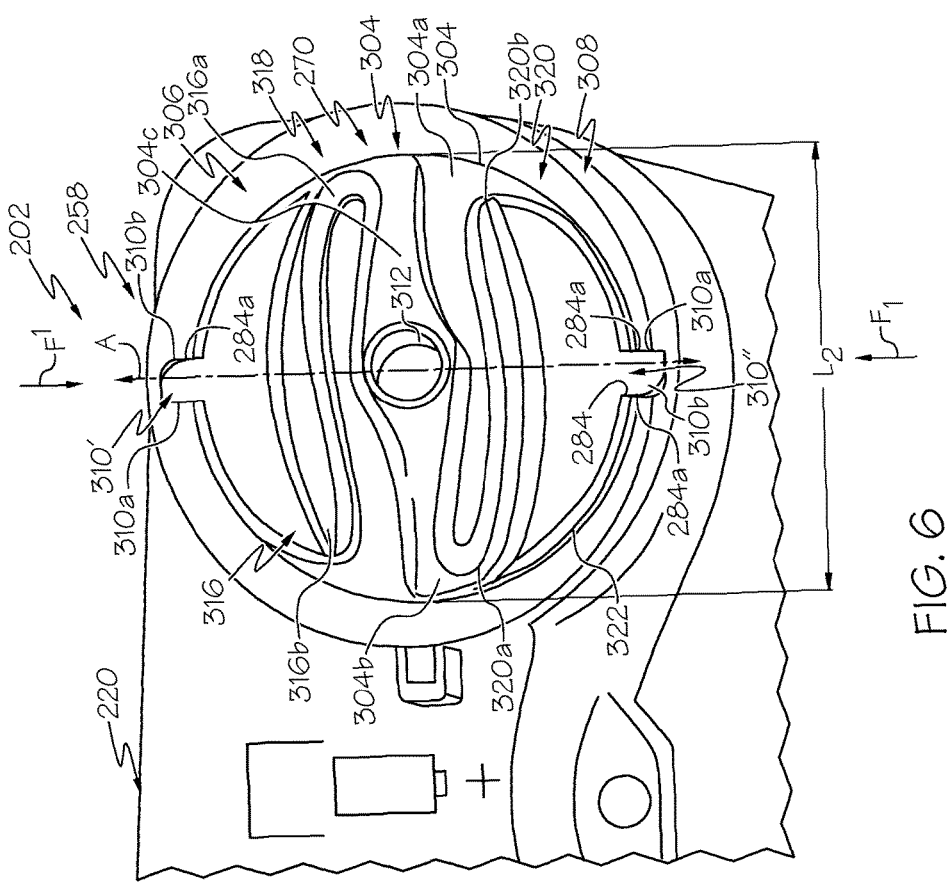

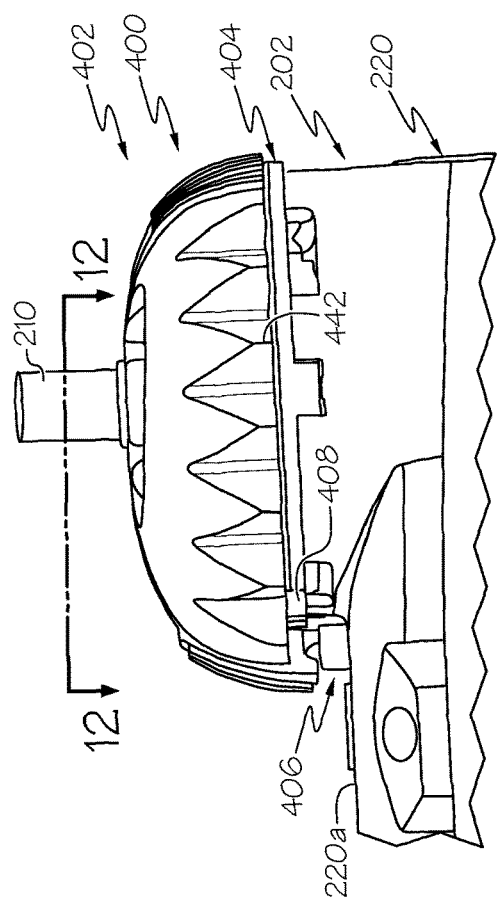
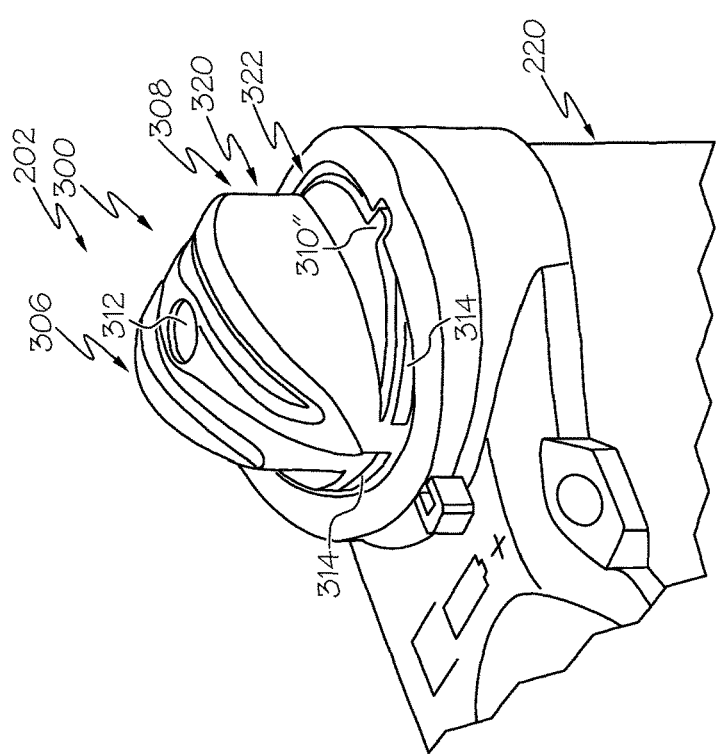
FIG. 9
FIG. 8

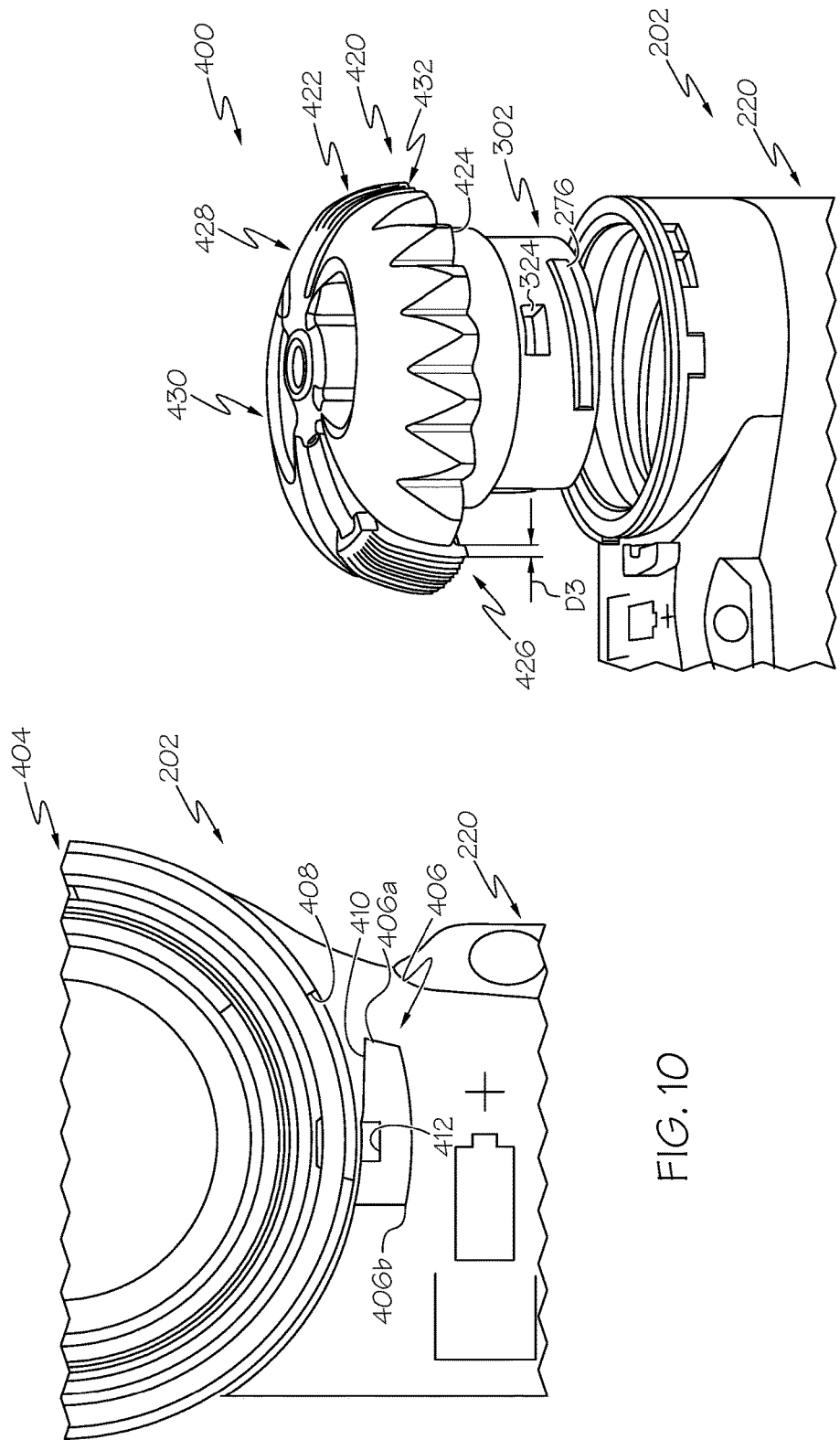

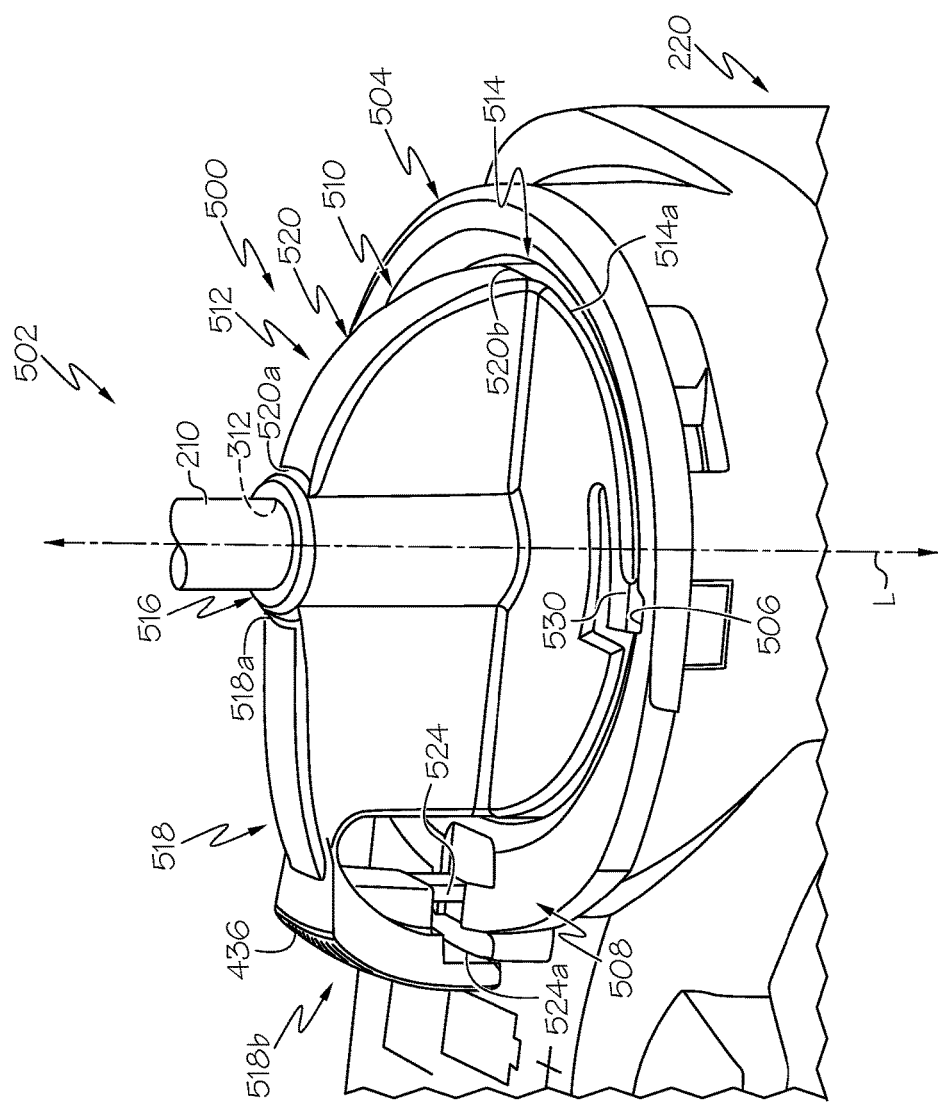

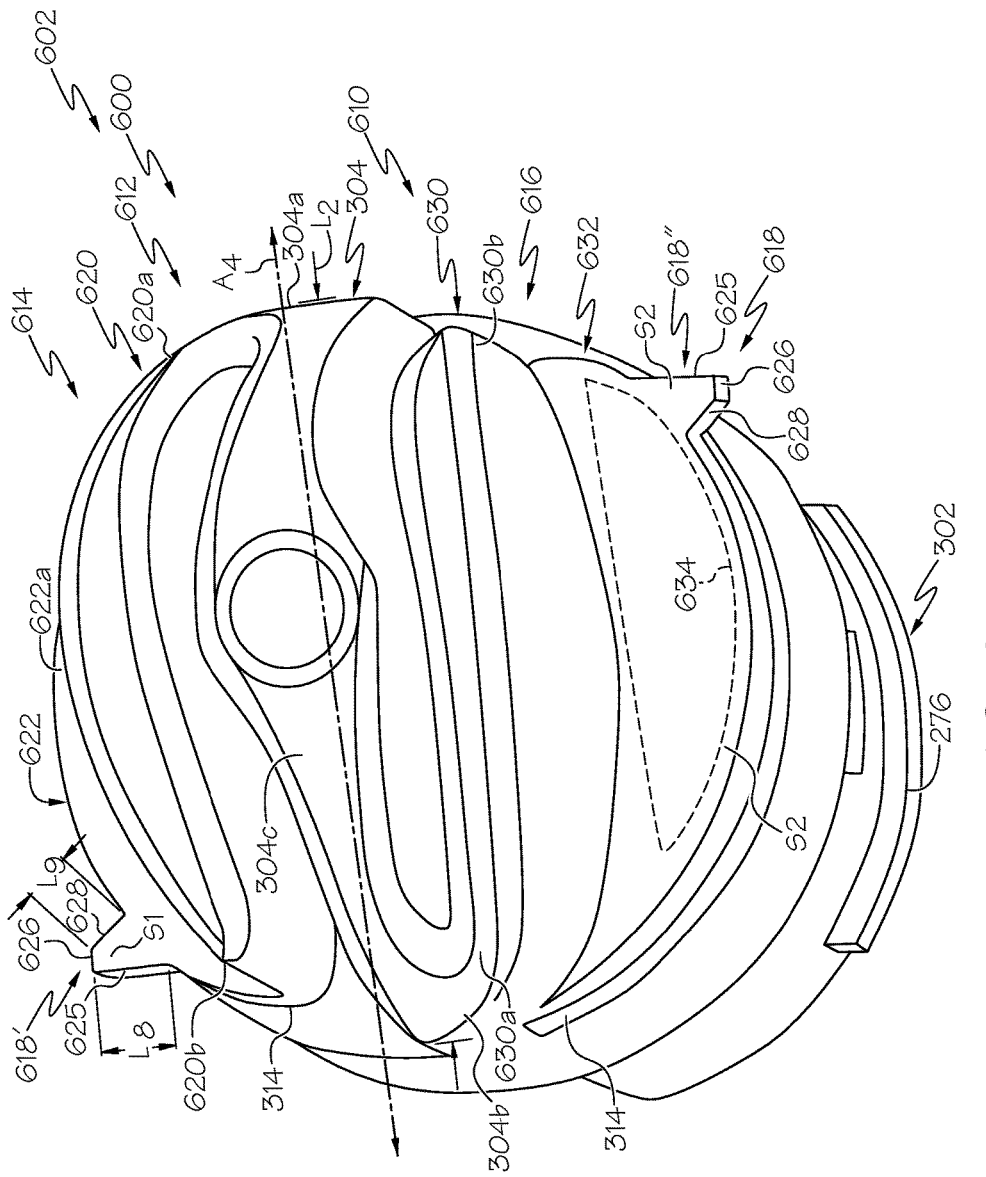

SYSTEMS FOR SET CONNECTOR ASSEMBLY WITH LOCK

TECHNICAL FIELD

Embodiments of the subject matter described herein relate generally to fluid infusion devices for delivering a medication fluid to the body of a user. More particularly, embodiments of the subject matter relate to systems for a fluid infusion device having a set connector assembly with a lock.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a suitable hollow tubing. In certain instances, the hollow tubing is coupled to the external fluid infusion device by a set connector assembly. For external infusion devices for ambulatory or portable use, the set connector assembly may inadvertently move during a movement of the user.

Accordingly, it is desirable to provide systems for a set connector assembly with a lock for use with a fluid infusion device. Furthermore, other desirable features and characteristics will become apparent from the subsequent detailed description and the appended claims, taken in conjunction with the accompanying drawings and the foregoing technical field and background.

BRIEF SUMMARY

According to various embodiments, provided is a set connector assembly for a fluid infusion device. The set connector assembly includes a connector having a body. The body defines a graspable portion and a coupling portion, and the coupling portion is to be received within a portion of the fluid infusion device. The graspable portion has at least one locking tab to lock the connector to the fluid infusion device, and the graspable portion is movable relative to the body to move the connector between a first, locked position and a second, unlocked position relative to the fluid infusion device.

Further provided is a fluid infusion device. The fluid infusion device includes a housing that includes a lock, and a set connector assembly removably coupled to the housing to define a fluid flow path from the fluid infusion device. The set connector assembly includes a connector having a body. The body defines a graspable portion and a coupling portion. The coupling portion is receivable within the housing. The graspable portion has at least one locking tab that engages the lock, and the graspable portion is movable relative to the body to move the connector between a first, locked position and a second, unlocked position relative to the housing.

Also provided is a fluid infusion device. The fluid infusion device includes a housing having an opening that receives a fluid reservoir. The housing includes a lock. The fluid infusion device includes a set connector assembly removably coupled to the housing to define a fluid flow path from the fluid reservoir. The set connector assembly includes a connector having a body. The body defines a graspable portion and a coupling portion. The coupling portion is receivable within the housing and positionable about the fluid reservoir to define the fluid flow path. The graspable portion has a locking arm that defines a locking tab that engages the lock. The graspable portion is movable relative to the body to move the connector between a first, locked position and a second, unlocked position relative to the housing.

According to various embodiments, also provided is a set connector assembly for a fluid infusion device. The set connector assembly includes a connector having a body. The body defines a graspable portion and a coupling portion, and the coupling portion is to be received within a portion of the fluid infusion device. The graspable portion has at least one wing that defines at least one locking tab for locking the connector to the fluid infusion device. The graspable portion is movable relative to the body to move the connector between a first, locked position and a second, unlocked position relative to the fluid infusion device.

Further provided is a set connector assembly for a fluid infusion device. The set connector assembly includes a connector having a body that defines a graspable portion and a coupling portion. The coupling portion is to be received within a portion of the fluid infusion device. The graspable portion includes a first wing that defines a first locking tab to lock the connector to the fluid infusion device; a second wing that defines a second locking tab to lock the connector to the fluid infusion device; and a main branch having a first end and a second end. The first wing is coupled to the first end and the second wing is coupled to the second end. The main branch couples the graspable portion to the coupling portion such that a gap is defined between the first wing and the coupling portion and the second wing and the coupling portion. The graspable portion is movable relative to the body to move the connector between a first, locked position and a second, unlocked position relative to the fluid infusion device.

Also provided according to various embodiments is a fluid infusion device. The fluid infusion device includes a housing that includes a lock and a set connector assembly removably coupled to the housing to define a fluid flow path from the fluid infusion device. The set connector assembly includes a connector having a body that defines a graspable portion and a coupling portion. The coupling portion is receivable within the housing, and the graspable portion has at least one wing that defines a locking tab for engaging the lock. The at least one wing is movable relative to the body to disengage the locking tab with the lock.

Further provided is a fluid infusion device. The fluid infusion device includes a fluid reservoir and a housing that includes an opening that receives the fluid reservoir. The fluid infusion device includes a retaining ring coupled to the housing about the opening that includes at least one lock. The fluid infusion device also includes a set connector assembly removably coupled to the housing to define a fluid flow path from the fluid infusion device. The set connector assembly includes a connector having a body that defines a graspable portion and a coupling portion. The coupling portion is receivable within the housing and is coupled to the fluid reservoir. The graspable portion includes at least one wing that defines a locking tab for engaging the at least one lock. The connector is movable relative to the housing between a first position, in which the locking tab engages the at least one lock to retain the fluid reservoir within the housing, and a second position, in which the locking tab is disengaged from the at least one lock to enable the removal of the fluid reservoir from the housing.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 4 is an end view of a portion of the fluid infusion device of FIG. 2, with a connector of the set connector assembly shown in a second, unlocked position relative to a housing of the fluid infusion device;

FIG. 5 is a top perspective view of a retaining ring associated with the housing of the fluid infusion device of FIG. 2;

FIG. 6 is a top view of a portion of the fluid infusion device of FIG. 2, with the connector of the set connector assembly shown in a first, locked position relative to the housing of the fluid infusion device;

FIG. 7 is a side view of a portion of the fluid infusion device of FIG. 2, with the connector of the set connector assembly of FIG. 4 in the second, unlocked position relative to the housing of the fluid infusion device;

FIG. 8 is a perspective view of a portion of the fluid infusion device of FIG. 2, with the connector of the set connector assembly of FIG. 4 in the second, unlocked position;

FIG. 9 is a side view of a portion of the fluid infusion device of FIG. 2, with a connector of an exemplary set connector assembly in a first, locked position relative to the housing of the fluid infusion device in accordance with the various teachings of the present disclosure;

FIG. 10 is a top perspective view of an exemplary retaining ring, which is associated with the housing of the fluid infusion device of FIG. 2 in accordance with various embodiments;

FIG. 11 is a perspective view of a portion of the fluid infusion device of FIG. 2, with the connector of the set connector assembly of FIG. 9 shown in a second, unlocked position relative to the housing of the fluid infusion device;

FIG. 14 is a side view of a portion of the fluid infusion device of FIG. 2, with a connector of an exemplary set connector assembly in a first, locked position relative to the housing of the fluid infusion device in accordance with the various teachings of the present disclosure;

FIG. 19 is a perspective view of the connector of FIG. 17, in which the exemplary marking are removed for clarity.

DETAILED DESCRIPTION

Figure 1:
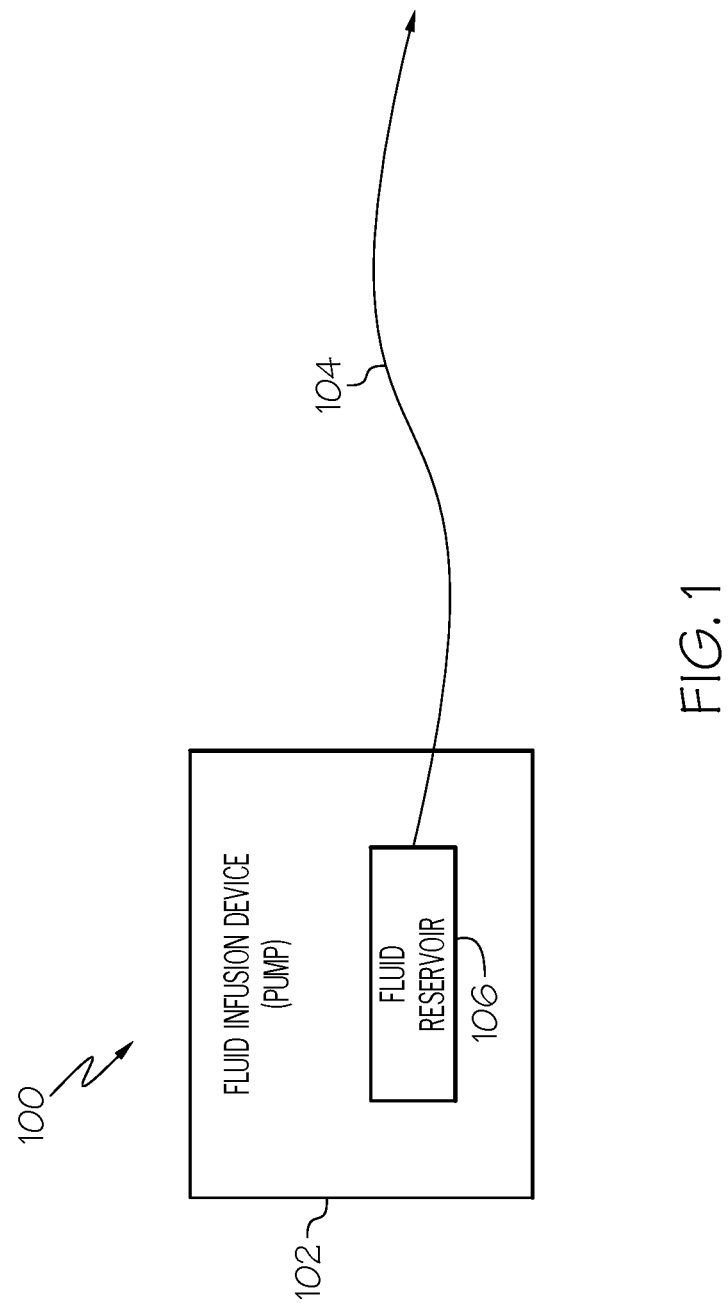
FIG. 1 is a simplified block diagram representation of an embodiment of a fluid delivery system according to various embodiments.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

FIG. 1 is a simplified block diagram representation of an embodiment of a fluid delivery system 100, which can be utilized to administer a medication fluid such as insulin to a patient. The fluid delivery system 100 includes a fluid infusion device 102 (e.g., an infusion pump) and a fluid conduit assembly 104 that is coupled to, integrated with, or otherwise associated with the fluid infusion device 102. The fluid infusion device 102 includes a fluid reservoir 106 or an equivalent supply of the medication fluid to be administered. The fluid infusion device 102 is operated in a controlled manner to deliver the medication fluid to the user via the fluid conduit assembly 104. Although not depicted in FIG. 1, the fluid delivery system 100 also includes set connector assembly with a lock that couples the fluid conduit assembly 104 to the fluid reservoir 106.

Figure 2:
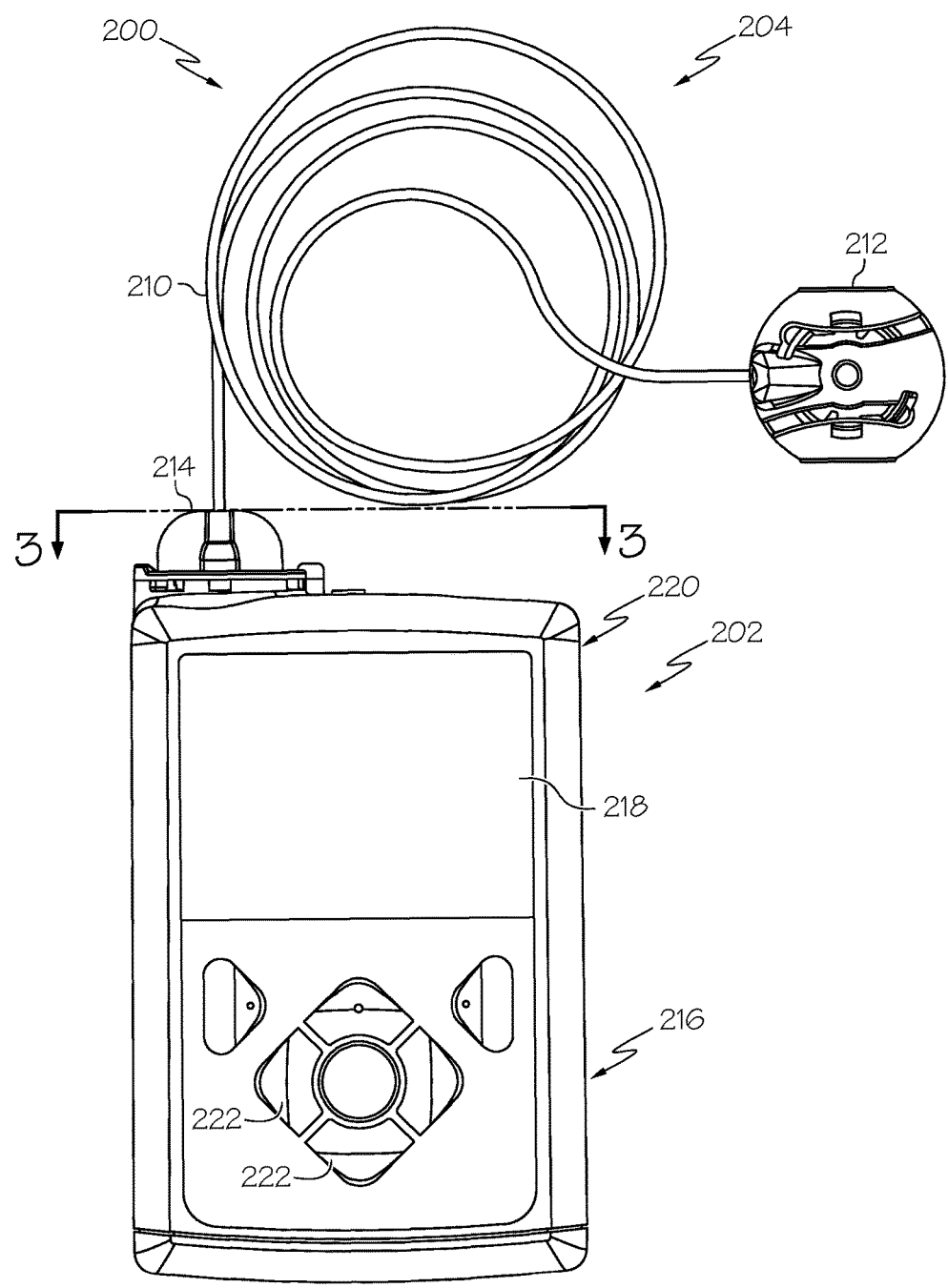
FIG. 2 is a plan view of an exemplary embodiment of a fluid delivery system that includes a fluid infusion device having an exemplary set connector assembly with a lock and an infusion set according to the various teachings of the present disclosure.

The fluid infusion device 102 may be provided in any desired configuration or platform. In accordance with one non-limiting embodiment, the fluid infusion device is realized as a portable unit that can be carried or worn by the patient. In this regard, FIG. 2 is a plan view of an exemplary embodiment of a fluid delivery system 200 that includes a portable fluid infusion device 202 and a fluid conduit assembly that takes the form of an infusion set component 204. The infusion set component 204 is coupled to the fluid infusion device 202. The fluid infusion device 202 accommodates a fluid reservoir (shown in FIG. 3) for the medication fluid to be delivered to the user.

The illustrated embodiment of the infusion set component 204 includes, without limitation: a tube 210; an infusion unit 212 coupled to the distal end of the tube 210; and a set connector or set connector assembly 214 coupled to the proximal end of the tube 210. The infusion set component 204 defines a fluid flow path that fluidly couples the fluid reservoir to the infusion unit 212. The fluid infusion device 202 is designed to be carried or worn by the patient, and the infusion set component 204 terminates at the infusion unit 212 such that the fluid infusion device 202 can deliver fluid to the body of the patient via the tube 210. The fluid infusion device 202 may leverage a number of conventional features, components, elements, and characteristics of existing fluid infusion devices. For example, the fluid infusion device 202 may incorporate some of the features, components, elements, and/or characteristics described in U.S. Pat. Nos. 6,485,465 and 7,621,893, the relevant content of which is incorporated by reference herein.

In this example, the fluid infusion device 202 includes a user interface 216 and a display 218 coupled to a housing 220. The user interface 216 includes one or more input devices 222, which can be activated by the user. The user interface 216 can be used to administer a bolus of insulin, to change therapy settings, to change user preferences, to select display features, and the like. Although not required, the illustrated embodiment of the fluid infusion device 202 includes the display 218. The display 218 can be used to present various types of information or data to the user, such as, without limitation: the current glucose level of the patient; the time; a graph or chart of the patient's glucose level versus time; device status indicators, etc. In some embodiments, the display 218 is realized as a touch screen display element and, therefore, the display 218 also serves as a user interface component.

Figure 3:
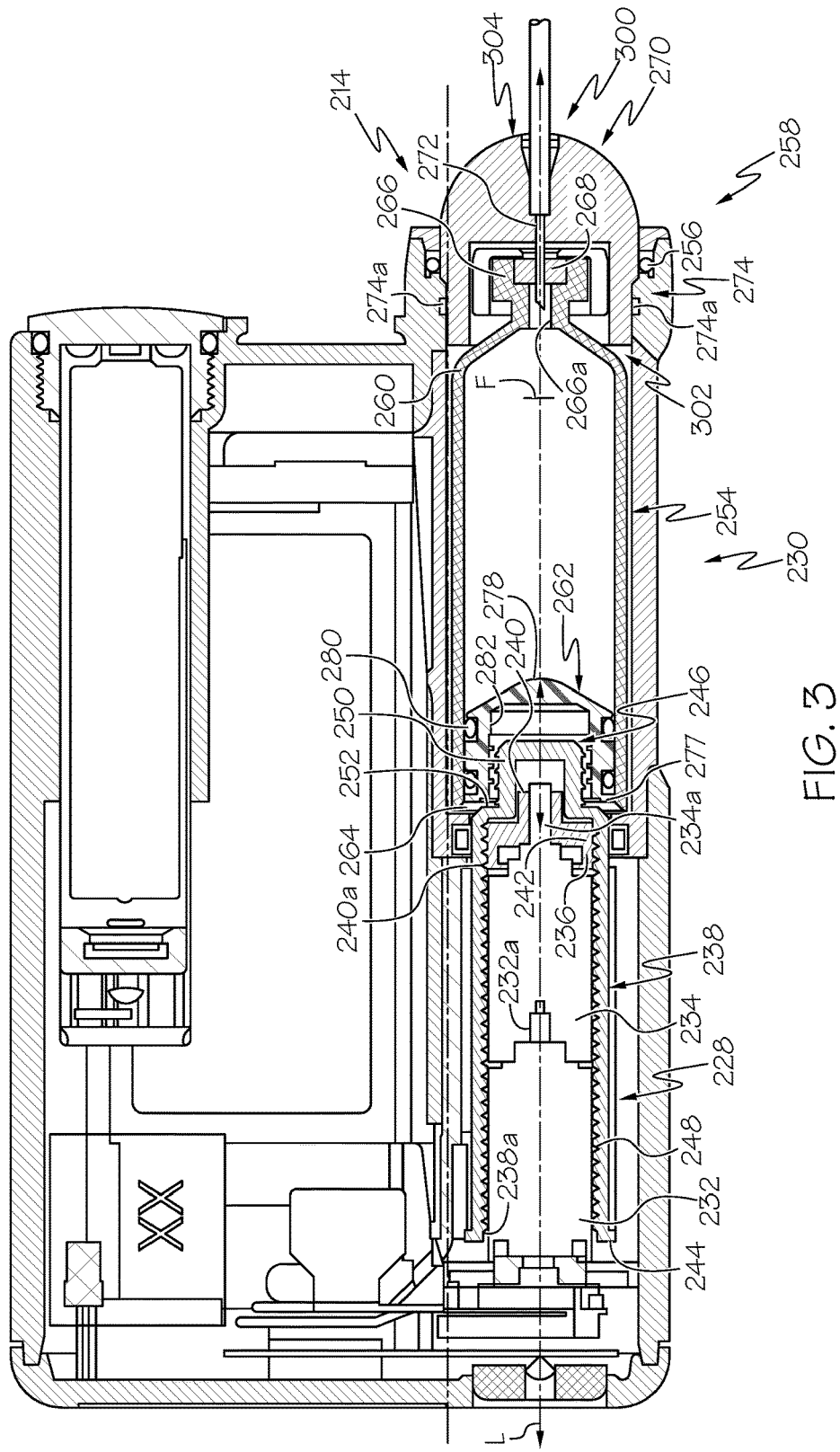
FIG. 3 is a cross-sectional view of the fluid infusion device of FIG. 2, taken along line 3-3 of FIG. 2.

With reference to FIG. 3, the housing 220 of the fluid infusion device 202 accommodates a power supply 224, a controller or control module 226, a drive system 228 and a fluid reservoir system 230. Generally, the power supply 224, the control module 226 and the drive system 228 are accommodated in a pump chamber defined by the housing 220, and the fluid reservoir system 230 is accommodated in a reservoir chamber defined by the housing 220.

The power supply 224 is any suitable device for supplying the fluid infusion device 202 with power, including, but not limited to, a battery. In one example, the power supply 224 can be removable relative to the housing 220; however, the power supply 224 can also be fixed within the housing 220. The control module 226 is in communication with the user interface 216, display 218, power supply 224 and drive system 228. The control module 226 controls the operation of the fluid infusion device 202 based on patient specific operating parameters. For example, the control module 226 controls the supply of power from the power supply 224 to the drive system 228 to activate the drive system 124 to dispense fluid from the fluid reservoir system 230. Further detail regarding the control of the fluid infusion device 202 can be found in U.S. Pat. Nos. 6,485,465 and 7,621,893, the relevant content of which was previously incorporated herein by reference.

The drive system 228 cooperates with the fluid reservoir system 230 to dispense the fluid from the fluid reservoir system 230. In one example, the drive system 228 includes a motor 232, a gear box 234, a drive screw 236 and a slide 238. The motor 232 receives power from the power supply 224 as controlled by the control module 226. In one example, the motor 232 is an electric motor. The motor 232 includes an output shaft 232a. The output shaft 232a is coupled to the gear box 234. In one embodiment, the gear box 234 is a reduction gear box. The gear box 234 includes an output shaft 234a, which is coupled to the drive screw 236.

The drive screw 236 includes a generally cylindrical distal portion 240 and a generally cylindrical proximal portion 242. The distal portion 240 has a diameter, which can be larger than a diameter of the proximal portion 242. The distal portion 240 includes a plurality of threads 240a. The plurality of threads 240a are generally formed about an exterior circumference of the distal portion 240. The proximal portion 242 is generally unthreaded, and can be sized to be received within a portion of the slide 238. The proximal portion 242 can serve to align the drive screw 236 within the slide 238 during assembly, for example.

With continued reference to FIG. 3, the slide 238 is substantially cylindrical and includes a distal slide end 244, a proximal slide end 246 and a plurality of threads 248. The distal slide end 244 is adjacent to the motor 232 when the slide 238 is in a first, fully retracted position and the proximal slide end 246 is adjacent to the drive screw 236 when the slide 238 is in the first, fully retracted position. The proximal slide end 246 includes a projection 250 and a shoulder 252, which cooperate with the fluid reservoir system 230 to dispense the fluid from the fluid reservoir system 230. The shoulder 252 is defined adjacent to the projection 250 and contacts a portion of the fluid reservoir system 230 to dispense fluid from the fluid reservoir system 230.

The plurality of threads 248 of the slide 238 are formed along an interior surface 238a of the slide 238 between the distal slide end 244 and the proximal slide end 246. The plurality of threads 248 are formed so as to threadably engage the threads 240a of the drive screw 236. Thus, the rotation of the drive screw 236 causes the linear translation of the slide 238.

In this regard, the slide 238 is generally sized such that in a first, retracted position, the motor 232, the gear box 234 and the drive screw 236 are substantially surrounded by the slide 238. The slide 238 is movable to a second, fully extended position through the operation of the motor 232. The slide 238 is also movable to a plurality of positions between the first, retracted position and the second, fully extended position via the operation of the motor 232. Generally, the operation of the motor 232 rotates the output shaft 232a, which is coupled to the gear box 234. The gear box 234 reduces the speed and increases the torque output by the motor 232, and the output shaft 234a of the gear box 234 rotates the drive screw 236, which moves along the threads 248 formed within the slide 238. The movement or rotation of the drive screw 236 relative to the slide 238 causes the movement or linear translation of the slide 238 within the housing 220. The forward advancement of the slide 238 (i.e. the movement of the slide 238 toward the fluid reservoir system 230) causes the fluid reservoir system 230 to dispense fluid.

With continued reference to FIG. 3, the fluid reservoir system 230 includes a fluid reservoir 254, a sealing member 256 and a retaining ring 258. The fluid reservoir 254 and the sealing member 256 are each received within an opening defined by the housing 220, and the retaining ring 258 is coupled about the opening. The sealing member 256 is coupled between the fluid reservoir 254 and the retaining ring 258 to prevent the ingress of fluids into the fluid reservoir chamber of the housing 220. In one example, the sealing member 256 comprises an O-ring; however, any suitable device can be used to prevent the ingress of fluids, as known to one skilled in the art.

With reference to FIG. 3, the fluid reservoir 254 includes a body or barrel 260 and a stopper 262. The barrel 260 has a first or distal barrel end 264 and a second or proximal barrel end 266. Fluid F is retained within the barrel 260 between the distal barrel end 264 and the proximal barrel end 266. The distal barrel end 264 is positioned adjacent to the slide 238 when the fluid reservoir 254 is assembled in the housing 220. Generally, the distal barrel end 264 can have a substantially open perimeter or can be substantially circumferentially open such that the slide 238 is receivable within the barrel 260 through the distal barrel end 264.

The proximal barrel end 266 can have any desirable size and shape configured to mate with at least a portion of the set connector assembly 214, as will be discussed in further detail herein. In one example, the proximal barrel end 266 defines a passageway 226a through which the fluid F flows out of the fluid reservoir 254. The passageway 226a is closed by a septum 268. The septum 268 is received within a portion of the proximal barrel end 266, and is coupled to the proximal barrel end 266 through any suitable technique, such as ultrasonic welding, press-fit, etc. The septum 268 serves as a barrier to prevent the ingress of fluids into the fluid reservoir system 230, and prevents the egress of fluids from the fluid reservoir 254. The septum 268 is pierceable by the set connector assembly 214 to define a fluid flow path out of the fluid reservoir 254. In one example, the set connector assembly 214 includes a connector 270, a hollow instrument or needle 272 and the tube 210. As will be discussed, the connector 270 couples the needle 272 and the tube 210 to the fluid reservoir 254, and locks into place once coupled to the fluid reservoir 254 to maintain the fluid flow path between the fluid reservoir 254 and the infusion unit 212 (FIG. 2). The needle 272 defines a flow path for the fluid F out of the fluid reservoir 254, through the connector 270 and into the tube 210.

In one example, the housing 220 includes a retaining system 274, which couples the set connector assembly 214 to the fluid reservoir 254. In one example, the retaining system 274 comprises one or more threads 274a. The one or more threads 274a threadably engage corresponding threads 276 (FIG. 4) defined in the connector 270 to couple the connector 270 to the fluid reservoir 254.

With reference to FIG. 3, the stopper 262 is disposed within the barrel 260. The stopper 262 is movable within and relative to the barrel 260 to dispense fluid from the fluid reservoir 254. When the barrel 260 is full of fluid, the stopper 262 is adjacent to the distal barrel end 264, and the stopper 262 is movable to a position adjacent to the proximal barrel end 266 to empty the fluid from the fluid reservoir 254. In one example, the stopper 262 is substantially cylindrical, and includes a distal stopper end 277, a proximal stopper end 278, at least one friction element 280 and a counterbore 282 defined from the distal stopper end 277 to the proximal stopper end 278.

The distal stopper end 277 is open about a perimeter of the distal stopper end 277, and thus, is generally circumferentially open. The proximal stopper end 278 is closed about a perimeter of the proximal stopper end 278, and thus, is generally circumferentially closed. The proximal stopper end 278 includes a slightly conical external surface, however, the proximal stopper end 278 can be flat, convex, etc. The at least one friction element 280 is coupled to the stopper 262 about an exterior surface of the stopper 262. In one example, the at least one friction element 280 comprises two friction elements, which include, but are not limited to, O-rings. The friction elements 280 are coupled to circumferential grooves defined in the exterior surface of the stopper 262.

The counterbore 282 receives the projection 250 of the slide 238 and the movement of the slide 238 causes the shoulder 252 of the slide 238 to contact and move the stopper 262. In one example, the counterbore 282 includes threads; however, the projection 250 of the slide 238 is not threadably engaged with the stopper 262. Thus, the threads illustrated herein are merely exemplary.

The retaining ring 258 cooperates with the set connector assembly 214 to aid in coupling the connector 270 to the fluid reservoir 254, as will be discussed in greater detail herein. The retaining ring 258 is coupled to a portion of the housing 220 and substantially surrounds the opening defined in the housing 220 that receives the fluid reservoir 254. The retaining ring 258 is coupled to the housing 220 about the opening such that the sealing member 256 is disposed between the housing 220 and the retaining ring 258. For example, the retaining ring 258 can be ultrasonically welded onto the housing 220; however, any suitable technique can be used to couple the retaining ring 258 to the housing 220, such as a press-fit, mechanical fasteners, etc. In one example, the retaining ring 258 is substantially annular; however, the retaining ring 258 can have any suitable shape that corresponds to the shape of the portion of the housing 220 that receives the fluid reservoir 254.

With reference to FIG. 4, the retaining ring 258 is illustrated without the set connector assembly 214 and the fluid reservoir 254. The retaining ring 258 includes one or more locks 284, which cooperate with the set connector assembly 214 to lock the set connector assembly 214 to the housing 220. In this example, the retaining ring 258 comprises two locks 284 that are positioned substantially opposite each other about a circumference of the retaining ring 258. It should be noted, however, that any number of locks 284 can be employed and the locks 284 can be positioned at any desired location about the circumference of the retaining ring 258. The locks 284 are substantially U-shaped pockets, and are sized to receive a portion of the set connector assembly 214. In this example, the locks 284 include a plurality of planar wall surfaces 284a and an arcuate surface 284b, which cooperate to define the locks 284. It should be noted, however, that the locks 284 can have any desired shape, and moreover, the locks 284 need not have the same shape. Further, the locks 284 can include one or more ramp surfaces, if desired. In this example, the planar wall surfaces 284a act as a stop for the portion of the set connector assembly 214, while the arcuate surface 284b provides clearance for the portion of the set connector assembly 214 within the locks 284.

With reference to FIG. 3, the set connector assembly 214 mates with and couples to the proximal barrel end 266 of the fluid reservoir 254, establishing the fluid path from the fluid reservoir 254 to the tube 210. The set connector assembly 214 (with the fluid reservoir 254 coupled thereto) is coupled to the housing 220 of the fluid infusion device 202 to seal and secure the fluid reservoir 254 inside the housing 220. Thereafter, actuation of the fluid infusion device 202 causes the medication fluid to be expelled from the fluid reservoir 254, through the infusion set component 204, and into the body of the patient via the infusion unit 212 at the distal end of the tube 210. Accordingly, when the set connector assembly 214 is installed as depicted in FIG. 3, the tube 210 extends from the fluid infusion device 202 to the infusion unit 212 and the needle 272 provides a fluid pathway to the body of the patient. For the illustrated embodiment, the set connector assembly 214 is realized as a removable reservoir cap (or fitting) that is suitably sized and configured to accommodate replacement of fluid reservoirs (which are typically disposable) as needed.

With reference to FIG. 4, the connector 270 of the set connector assembly 214 is shown in greater detail. In FIG. 4, the connector 270 is illustrated without the needle 272 and the tube 210 for clarity. The connector 270 is removably coupled to the housing 220 and retains the fluid reservoir 254 within the housing 220. Generally, the connector 270 is composed of a polymeric material, such as a polycarbonate material, and comprises a one-piece monolithic component; however, the connector 270 can be composed of any suitable material and can be assembled from multiple components. In the example of a monolithic polymeric component, the connector 270 can be formed through injection molding, or 3D printing, for example. The connector 270 has a body 298, which defines a graspable portion 300 and a coupling portion 302. The graspable portion 300 is movable relative to the body 298 to move the connector 270 between a first, locked position and a second, unlocked position relative to the housing 220.

The graspable portion 300 includes a main branch 304, a first wing 306 and a second wing 308. The main branch 304 extends from the coupling portion 302 and couples the graspable portion 300 to the coupling portion 302. One or more of the first wing 306 and the second wing 308 define a locking tab 310. In this example, the first wing 306 defines a locking tab 310', and the second wing 308 defines a locking tab 310". The locking tabs 310', 310" are substantially similar on both the first wing 306 and the second wing 308; however, it should be understood that the locking tabs 310', 310" need not be substantially identical. With reference to FIG. 6, the graspable portion 300 is generally mirror symmetric about an axis A.

The main branch 304 defines a bore 312, which receives the needle 272 and the tube 210 (FIG. 3). In one example, the needle 272 and the tube 210 are coupled to the bore 312 through any desired technique, such as ultrasonic welding, adhesive bonding, etc. As illustrated in FIG. 4, the bore 312 is generally defined along a longitudinal axis L of the body 298 of the connector 270. The main branch 304 generally extends away from the coupling portion 302 to define a gap 314 between the first wing 306 and the second wing 308. The gap 314 enables the first wing 306 and the second wing 308 to move relative to the main branch 304, thereby engaging or disengaging the locking tabs 310', 310", as will be discussed in greater detail herein. Stated another way, the main branch 304 couples the graspable portion 300 to the coupling portion 302 such that the gap 314 is defined between the first wing 306, the second wing 308 and the coupling portion 302. In other words, the first wing 306 and the second wing 308 are not coupled to the coupling portion 302, but rather, the first wing 306 and the second wing 308 are movable relative to the coupling portion 302 and are each coupled solely to the main branch 304.

With reference back to FIG. 6, the main branch 304 includes a first end 304a and an opposite, second end 304b. The first wing 306 is coupled to the first end 304a, and the second wing 308 is coupled to the second end 304b. Generally, the first wing 306 is coupled to the first end 304a such that the first wing 306 extends from the first end 304a in a first direction towards the second end 304b of the main branch 304, and the second wing 308 is coupled to the second end 304b such that the second wing 308 extends from the second end 304b in a second direction towards the first end 304a. The second direction is different than the first direction, and in this example, is substantially opposite the first direction.

The first wing 306 includes a first arm 316 and a first flange 318. The first arm 316 is coupled to the first end 304a, and extends upwardly from the first flange 318 so as to be adjacent to a top surface 304c of the main branch 304. The first arm 316 is substantially arcuate, and includes a first arm end 316a and a second arm end 316b. The first arm end 316a is coupled to the first end 304a at a living hinge. The second arm end 316b extends from the first arm end 316a, in a direction toward the second end 304b of the main branch 304. Generally, the second arm end 316b does not extend to the second end 304b, but rather, extends for a length that is different than, and for example, less than, a length L2 of the main branch 304. The first flange 318 is coupled to the first arm 316 and extends along the first arm 316 from the first arm end 316a to the second arm end 316b, as illustrated in FIG. 7. As shown in FIGS. 4 and 7, the first flange 318 is adjacent to the gap 314. Generally, the first flange 318 extends outwardly from the first arm 316 along an axis, which is transverse to the longitudinal axis L, and in one example, is substantially perpendicular to the longitudinal axis L. The first flange 318 is generally semi-circular, and defines the locking tab 310'. The locking tab 310' extends outwardly from the first flange 318 so as to extend beyond a perimeter of the body 298 of the connector 270. Generally, the at least one locking tab 310' is defined on a perimeter of the first flange 318 so as to be defined between the first arm end 316a and the second arm end 316b. Stated another way, the at least one locking tab 310' is defined on the first flange 318 so as to be positioned between a first end of the first flange 318, with the first end of the first flange 318 coupled to the first arm end 316a, and a second end of the first flange 318, with the second end of the first flange 318 coupled to the second arm end 316b.

With reference to FIG. 6, the locking tab 310' has a planar surface 310a and an arcuate surface 310b. The planar surface 310a cooperates with one of the plurality of planar wall surfaces 284a of a respective one of the locks 284 to prevent the further rotation of the connector 270 relative to the housing 220. The arcuate surface 310b cooperates with the other of the plurality of planar wall surfaces 284a of the respective one of the locks 284 to assist in guiding the locking tab 310' out of engagement with the respective one of the locks 284 when the connector 270 is moved from the first, locked position to the second, unlocked position, as will be discussed further herein.

The second wing 308 includes a second arm 320 and a second flange 322. The second arm 320 is coupled to the second end 304b, and extends upwardly from the second flange 322 so as to be adjacent to the top surface 304c of the main branch 304. The second arm 320 is substantially arcuate, and includes a third arm end 320a and a fourth arm end 320b. The third arm end 320a is coupled to the second end 304b at a living hinge. The fourth arm end 320b extends from the third arm end 320a, in a direction toward the first end 304a of the main branch 304. Generally, the fourth arm end 320b does not extend to the first end 304a, but rather, extends for a length that is different than, and for example, less than, the length L2 of the main branch 304. The second flange 322 is coupled to the second arm 320 and extends along the second arm 320 from the third arm end 320a to the fourth arm end 320b. As illustrated in FIG. 4, the second flange 322 is adjacent to the gap 314. Generally, the second flange 322 extends outwardly from the second arm 320 along an axis, which is transverse to the longitudinal axis L, and in one example, is substantially perpendicular to the longitudinal axis L. The second flange 322 is generally semi-circular, and defines the locking tab 310". The locking tab 310" extends outwardly from the second flange 322 so as to extend beyond a perimeter of the body 298 of the connector 270. Generally, the at least one locking tab 310" is defined on a perimeter of the second flange 322 so as to be defined between the third arm end 320a and the fourth arm end 320b. Stated another way, the at least one locking tab 310" is defined on the second flange 322 so as to be positioned between a first end of the second flange 322, with the first end of the second flange 322 coupled to the third arm end 320a, and a second end of the second flange 322, with the second end of the second flange 322 coupled to the fourth arm end 320b.

With reference to FIG. 6, the locking tab 310" has the planar surface 310a and the arcuate surface 310b. The planar surface 310a cooperates with one of the plurality of planar wall surfaces 284a of the respective one of the locks 284 to prevent the further rotation of the connector 270 relative to the housing 220. The arcuate surface 310b cooperates with the other of the plurality of planar wall surfaces 284a of the respective one of the locks 284 to assist in guiding the locking tab 310" out of engagement with the respective one of the locks 284 when the connector 270 is moved from the first, locked position to the second, unlocked position.

With reference to FIG. 4, the coupling portion 302 extends along the longitudinal axis L, and is substantially cylindrical. The coupling portion 302 includes the threads 276, which are positioned about a circumference of the coupling portion 302. The coupling portion 302 has a first end 302a coupled to the main branch 304, and an opposite, second end 302b. The first end 302a is generally circumferentially closed, to prevent fluids from flowing into and/or out of the housing 220. The second end 302b is generally circumferentially open, to enable the coupling portion 302 to be received about the proximal barrel end 266 of the fluid reservoir 254 (FIG. 3). With reference to FIG. 7, the coupling portion 302 can also define one or more recesses 324 about a perimeter or circumference of the coupling portion 302. The one or more recesses 324 cooperate with one or more tabs on the fluid reservoir 254 to couple the fluid reservoir 254 to the coupling portion 302. In this example, the fluid reservoir 254 is coupled to the coupling portion 302 by a bayonet style connection (i.e. push in and twist the connector 270 to couple the fluid reservoir 254 to the connector 270), however, any suitable technique can be employed to couple the fluid reservoir 254 to the connector 270.

With reference to FIG. 3, with the housing 220 assembled with the power supply 224, the control module 226 and the drive system 228, the fluid reservoir system 230 can be coupled to the housing 220. In one example, a full fluid reservoir 254 is coupled to the set connector assembly 214. With the needle 272 and the tube 210 coupled to the connector 270, the axial insertion of the full fluid reservoir 254 into the connector 270 causes the needle 272 to pierce the septum 268, thereby defining a fluid flow path for the fluid F out of the fluid reservoir 254. The full fluid reservoir 254 is rotated relative to the connector 270, to couple the full fluid reservoir 254 to the coupling portion 302. With the fluid reservoir 254 coupled to the set connector assembly 214, the fluid reservoir 254 is inserted into the housing 220 such that the stopper 262 is adjacent to the projection 250 of the slide 238. The set connector assembly 214 is then coupled to the housing 220. In one example, with reference to FIG. 4, the coupling portion 302 is inserted into the housing 220 such that the threads 276 engage the threads 274a. The connector 270 is rotated, via the graspable portion 300, until the locking tabs 310', 310" engage with the respective locks 284. The engagement of the locking tabs 310', 310" with the respective locks 284 can provide tactile and audible feedback to the user that the connector 270 is locked to the housing 220.

With the locking tabs 310', 310" engaged with the respective locks 284, the connector 270, and thus, the set connector assembly 214, is secured or locked to the housing 220. With the set connector assembly 214 coupled to the fluid reservoir 254, one or more control signals from the control module 226 can drive the motor 232, thereby rotating the drive screw 236, which results in the linear translation of the slide 238. The advancement of the slide 238 into the fluid reservoir 254 moves the stopper 262, causing the fluid F to flow from the fluid reservoir 254 through the fluid flow path defined by the set connector assembly 214.

With reference to FIG. 8, the connector 270 is shown in the first, locked position, secured or locked to the housing 220. Thus, during movement of the user, the set connector assembly 214 is prevented or inhibited from inadvertently moving or rotating, thereby ensuring an uninterrupted fluid flow path from the fluid reservoir 254 through the tube 210. Stated another way, the connector 270 reduces and eliminates the need for an activity guard that locks over a portion of the housing 220 containing the fluid reservoir 254. In this regard, the locking tabs 310', 310" securely couple and lock the fluid reservoir 254 to and within the housing 220, thereby reducing and substantially eliminating the need for an additional guard against the inadvertent removal of the fluid reservoir 254.

In order to remove the set connector assembly 214, for example, to replace an empty fluid reservoir 254, with reference to FIG. 6, a force F1 can be applied to the first wing 306 and the second wing 308 to move the connector 270 from the first, locked position to the second, unlocked position. The application of the force F1 causes the first wing 306 and the second wing 308 to deflect inward, toward the main branch 304. The inward deflection of the first wing 306 and the second wing 308 causes the respective locking tab 310', 310" to move inward, thereby removing the locking tabs 310', 310" from the locks 284. With the locking tabs 310', 310" removed from the locks 284, the connector 270 can be rotated, for example, in a counterclockwise direction, and removed from the housing 220 or moved to the second, unlocked position.

With reference to FIG. 9, a connector 400 for use with a set connector assembly 402 is shown. The set connector assembly 402 can be used with the infusion set component 204 and the fluid infusion device 202 of FIG. 2, and can be used as an alternative to the set connector assembly 214. In this example, the fluid infusion device 202 includes a retaining ring 404 instead of the retaining ring 258 and a lock 406. Stated another way, the set connector assembly 402 necessitates the lock 406 to secure or lock the set connector assembly 402 to the housing 220 of the fluid infusion device 202. The remainder of the fluid infusion device 202 remains unchanged from that of FIGS. 1-8, and thus, only the differences in the fluid infusion device 202 associated with the use of the set connector assembly 402 will be discussed in detail herein. In this example, the retaining ring 404 is coupled to the housing 220, via ultrasonic welding, for example, to retain the sealing member 256 within the housing 220. Instead of including the locks 284, the retaining ring 404 includes a cut-out 408. The cut-out 408 enables the movement of a portion of the set connector assembly 402 relative to the housing 220. The cut-out 408 is defined along an exterior surface of the retaining ring 404 so as to be adjacent to the lock 406 when the retaining ring 404 is coupled to the housing 220.

The lock 406 is coupled to and extends upwardly from a surface 220a of the housing 220 so as to be adjacent to the fluid reservoir system 230. The lock 406 can be integrally formed with the housing 220, or can be coupled to the housing 220 via a suitable technique, such as ultrasonic welding, for example. With reference to FIG. 10, the housing 220 is illustrated without the set connector assembly 402 for clarity. The lock 406 includes a ramp surface 410 and a pocket 412. The ramp surface 410 is defined along a first end 406a of the lock 406, and has an increasing slope towards the pocket 412. The increasing slope assists in the uncoupling of the set connector assembly 402 from the housing 220. The pocket 412 is defined through the lock 406 at an end of the ramp surface 410, so as to be adjacent to a second end 406b of the lock 406. The pocket 412 has substantially planar walls, and is substantially U-shaped to receive a portion of the set connector assembly 402. While the housing 220 is illustrated herein as comprising a single lock 406, it will be understood that the housing 220 can include multiple locks 406, if desired.

With reference to FIG. 9, the set connector assembly 402 provides a fluid flow path from the fluid reservoir 254 to the user or patient. As the set connector assembly 402 can be similar to the set connector assembly 214 discussed with regard to FIGS. 1-8, the same reference numerals will be used to denote the same or similar components. In one example, the set connector assembly 402 includes the connector 400, the hollow instrument or needle 272 (not shown) and the tube 210. The connector 400 couples the needle 272 and the tube 210 to the fluid reservoir 254, and locks into place once coupled to the fluid reservoir 254 to maintain the fluid flow path between the fluid reservoir 254 and the infusion unit 212 (FIG. 2). The needle 272 defines a flow path for the fluid F out of the fluid reservoir 254, through the connector 400 and into the tube 210.

The set connector assembly 402 (with the fluid reservoir 254 coupled thereto) is coupled to the housing 220 of the fluid infusion device 202 to seal and secure the fluid reservoir 254 inside the housing 220. Thereafter, actuation of the fluid infusion device 202 causes the medication fluid to be expelled from the fluid reservoir 254, through the infusion set component 204, and into the body of the patient via the infusion unit 212 at the distal end of the tube 210. Accordingly, when the set connector assembly 402 is installed as depicted in FIG. 9, the tube 210 extends from the fluid infusion device 202 to the infusion unit 212 (FIG. 2), which in turn provides a fluid pathway to the body of the patient. For this embodiment, the set connector assembly 402 is realized as a removable reservoir cap (or fitting) that is suitably sized and configured to accommodate replacement of fluid reservoirs (which are typically disposable) as needed.

With reference to FIG. 11, the connector 400 of the set connector assembly 402 is shown in greater detail. In FIG. 11, the connector 400 is illustrated without the needle 272 and the tube 210 for clarity. The connector 400 is movably coupled to the housing 220 and retains the fluid reservoir 254 (FIG. 3) within the housing 220. Generally, the connector 400 is composed of a polymeric material, such as a polycarbonate material, and comprises a one-piece monolithic component; however, the connector 400 can be composed of any suitable material and can be assembled from multiple components. In the example of a monolithic polymeric component, the connector 400 can be formed through injection molding, or 3D printing, for example. The connector 400 has a body 420, which defines a graspable portion 422 and the coupling portion 302. The graspable portion 422 is movable relative to the body 420 to move the connector 400 between a first, locked position and a second, unlocked position relative to the housing 220.

Figure 12:
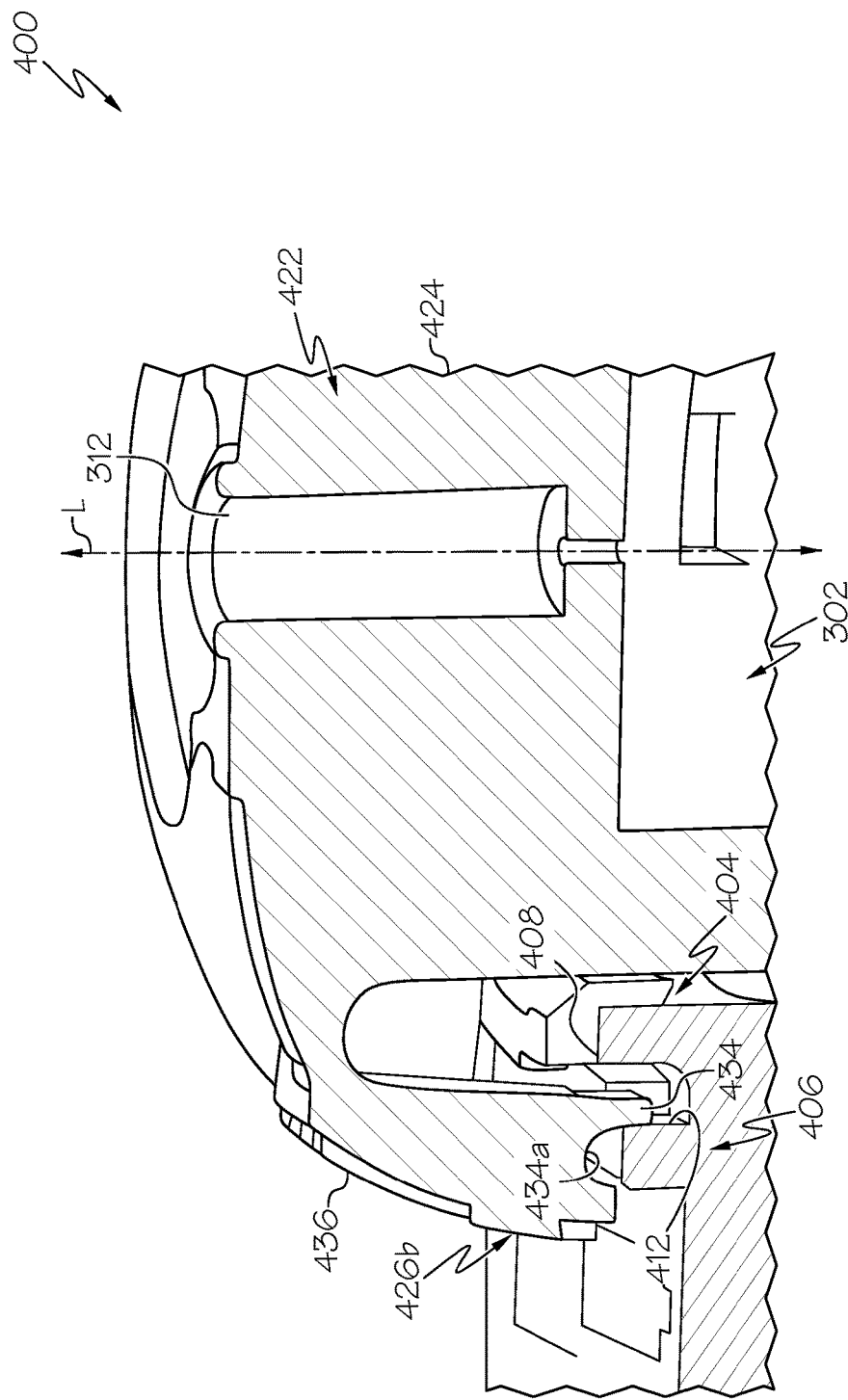
FIG. 12 is a cross-sectional view of the fluid infusion device and connector of FIG. 9, taken along line 12-12 of FIG. 9.

The graspable portion 422 includes a hub 424, a first, locking arm 426, a second arm 428, a first wing 430 and a second wing 432. The hub 424 is coupled to the coupling portion 302, and with reference to FIG. 12, is generally circumferentially closed to prevent the ingress of fluids into the housing 220. The hub 424 defines the bore 312, which receives the needle 272 and the tube 210 (FIG. 3). The bore 312 is generally defined along the longitudinal axis L of the connector 270.

Figure 13:
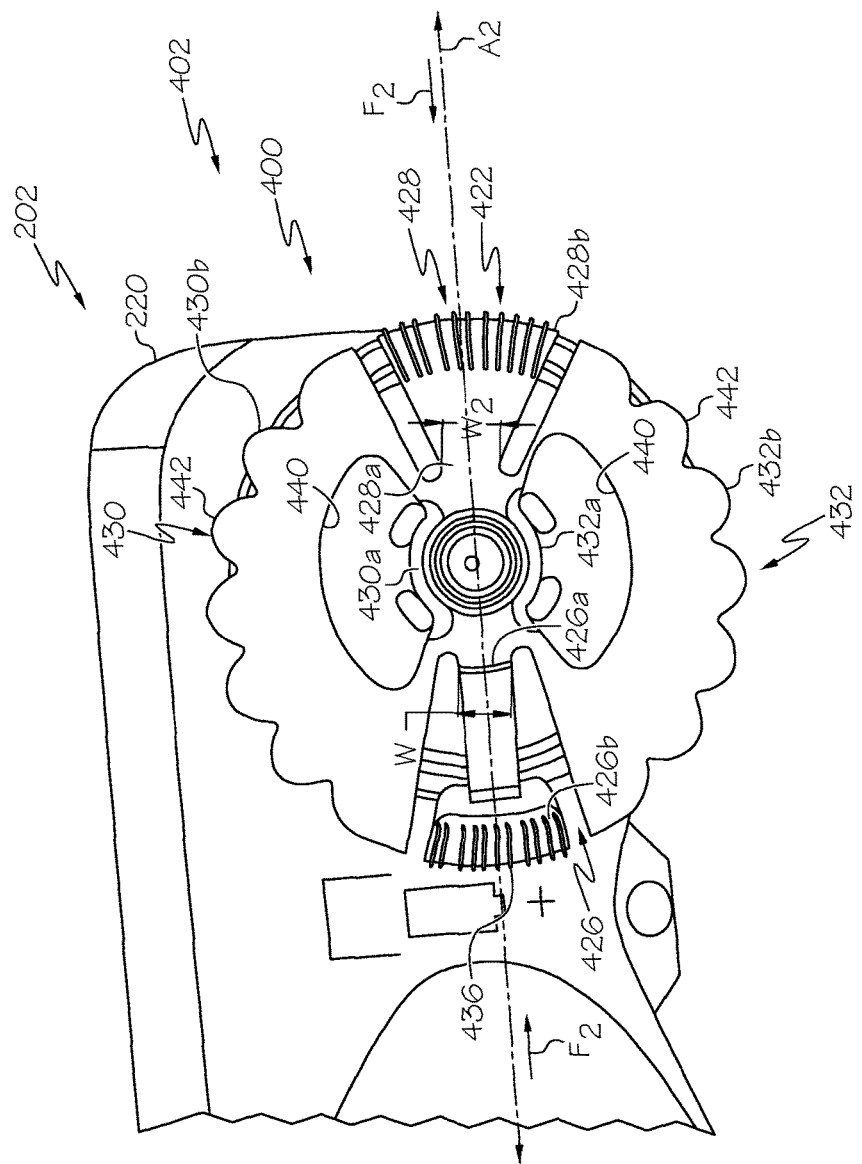
FIG. 13 is a top view of a portion of the fluid infusion device of FIG. 2, with the connector of the set connector assembly of FIG. 9 shown in the first, locked position relative to the housing of the fluid infusion device.

With reference to FIG. 13, the graspable portion 422 is generally symmetric relative to an axis A2. The locking arm 426 is coupled to the hub 424 so as to be substantially opposite the second arm 428 on the perimeter of the hub 424. The locking arm 426 extends outwardly from the hub 424, and includes a first end 426a and a second end 426b. Generally, only the first end 426a is coupled to the hub 424 to enable the locking arm 426 to move or deflect relative to the hub 424. In one example, the locking arm 426 generally has an arm width W, which is less than an arm width W2 of the second arm 428 to provide flexibility to the locking arm 426. With reference to FIG. 11, the locking arm 426 generally extends a distance D3 beyond a perimeter of the graspable portion 422 to provide a biasing force to lock the locking arm 426 into the lock 406 (via the compression of the locking arm 426). Similarly, the biasing force created by the locking arm 426 also resists the rotation of the locking arm 426 out of the pocket 412 of the lock 406.

With reference to FIG. 12, the second end 426b of the locking arm 426 cooperates with the lock 406 to lock the connector 400, and thus, the set connector assembly 402 to the housing 220. In one example, the second end 426b includes a locking tab 434 and a graspable surface 436. The locking tab 434 extends from the second end 426b to be received with in the pocket 412 defined by the lock 406. The locking tab 434 is generally rectangular, with a plurality of planar sides, which cooperate with the planar walls of the pocket 412 to prevent or inhibit the rotation of the connector 400 relative to the housing 220, thereby locking the set connector assembly 402 to the housing 220. A relief 434a may be defined adjacent to the locking tab 434 to facilitate the disengagement of the locking tab 434 with the pocket 412 by providing increased flexibility through the removal of material near the locking tab 434. The graspable surface 436 provides a roughened surface to aid a user in the movement of the connector 400 between the first, locked position and the second, unlocked position. In one example, the graspable surface 436 includes a plurality of striations; however, the graspable surface 436 can have any desired shape or texture.

With reference to FIG. 13, the second arm 428 is spaced apart from the locking arm 426 about the perimeter of the hub 424. The second arm 428 includes a third end 428a and a fourth end 428b. The third end 428a couples the second arm 428 to the hub 424. Generally, the second arm 428 is only coupled to the hub 424 via the third end 428a. The fourth end 428b defines a second graspable surface 438. The second graspable surface 438 comprises a plurality of striations, similar to the graspable surface 436. The graspable surface 436 and the second graspable surface 438 cooperate to define a pinch point or a point for the location of a force F2 by a user to move the connector 400 between the first, locked position and the second, unlocked position.

The first wing 430 is defined between the locking arm 426 and the second arm 428. In one example, the first wing 430 is defined about a portion of the perimeter of the connector 400 so as to be symmetrical with the second wing 432 relative to the axis A2. The first wing 430 includes a first wing end 430a and a second wing end 430b. The first wing end 430a is coupled to the hub 424, adjacent to the first end 426a and the third end 428a. In one example, a recess 440 is defined through a portion of the first wing 430 at or near the first wing end 430a. The recess 440 reduces a mass of the connector 400 and aids in the manufacturing of the connector 400. It should be noted that the recess 440 may be optional.

The first wing 430 also includes an undulating surface 442 at the second wing end 430b. The undulating surface 442 provides a graspable surface to aid the user in rotating the connector 400. It should be noted that the use of an undulating surface is merely exemplary, as the first wing 430 may have any suitable graspable surface, or may be smooth.

The second wing 432 is defined between the locking arm 426 and the second arm 428. The second wing 432 includes a third wing end 432a and a fourth wing end 432b. The first wing end 430a is coupled to the hub 424, adjacent to the first end 426a and the third end 428a. The second wing 432 includes the recess 440 defined through a portion of the second wing 432 at or near the third wing end 432a. The second wing 432 also includes the undulating surface 442 at the second wing end 430b.

With the housing 220 assembled, the set connector assembly 402, with the needle 272 and the tube 210 (FIG. 3) coupled to the connector 400, is then coupled to a full fluid reservoir 254. With the needle 272 and the tube 210 coupled to the connector 400, the axial insertion of the full fluid reservoir 254 into the connector 400 causes the needle 272 to pierce the septum 268, thereby defining a fluid flow path for the fluid F out of the fluid reservoir 254. The full fluid reservoir 254 is rotated relative to the connector 400 to couple the full fluid reservoir 254 to the coupling portion 302 (FIG. 3). The connector 400 and the fluid reservoir 254 are then inserted into the housing 220 such that the stopper 262 is adjacent to the projection 250 of the slide 238 (FIG. 3). In one example, with reference to FIG. 11, the coupling portion 302 is inserted into the housing 220 such that the threads 276 engage the threads 274a (FIG. 3). The connector 400 is rotated, via the undulating surface 442, until the locking tab 434 engages the pocket 412 of the lock 406. The engagement of the locking tab 434 with the pocket 412 of the lock 406 can provide tactile and audible feedback to the user that the connector 400 is locked to the housing 220. During the rotation of the connector 400, the locking tab 434 is guided along the cut-out 408 until the locking tab 434 snaps into place with the pocket 412 of the lock 406.

With the locking tab 434 engaged with the pocket 412, the connector 400, and thus, the set connector assembly 402, is secured or locked to the housing 220. With the set connector assembly 402 coupled to the fluid reservoir 254, one or more control signals from the control module 226 can drive the motor 232, thereby rotating the drive screw 236, which results in the linear translation of the slide 238 (FIG. 3). The advancement of the slide 238 into the fluid reservoir 254 moves the stopper 262, causing the fluid F to flow from the fluid reservoir 254 through the fluid flow path defined by the set connector assembly 402.

With reference to FIG. 13, the connector 400 is shown in the first, locked position, secured or locked to the housing 220. Thus, during movement of the user, the set connector assembly 402 is prevented or inhibited from inadvertently moving or rotating, thereby ensuring an uninterrupted fluid flow path from the fluid reservoir 254 through the tube 210.

In order to remove the set connector assembly 402, for example, to replace an empty fluid reservoir 254, with reference to FIG. 13, the force F2 can be applied to the locking arm 426 and the second arm 428, while rotating the graspable portion 422 to move the locking tab 434 out of the pocket 412 of the lock 406. Once the locking tab 434 is released from the pocket 412, the locking tab 434 follows the ramp surface 414 and the connector 400 is rotated, via the undulating surface 442, to remove the connector 400 from the housing 220 or move the connector 400 to the second, unlocked position.

With reference to FIG. 14, a connector 500 for use with a set connector assembly 502 is shown. The set connector assembly 502 can be used with the infusion set component 204 and the fluid infusion device 202 of FIG. 2, and can be used as an alternative to the set connector assembly 214. In this example, the fluid infusion device 202 includes a retaining ring 504 instead of the retaining ring 258. Stated another way, the set connector assembly 502 necessitates the retaining ring 504 to secure or lock the set connector assembly 502 to the housing 220 of the fluid infusion device 202. The remainder of the fluid infusion device 202 remains unchanged from that of FIGS. 1-8, and thus, only the differences in the fluid infusion device 202 associated with the use of the set connector assembly 502 will be discussed in detail herein. In this example, the retaining ring 504 is coupled to the housing 220, via ultrasonic welding, for example, to retain the sealing member 256 within the housing 220. The retaining ring 504 includes a pair of pockets 506 and a lock 508. The pair of pockets 506 receives a portion of the connector 500 to assist in coupling the connector 500 to the housing 220. The pockets 506 are generally defined so as to be located opposite of each other about the circumference of the retaining ring 504. The lock 508 receives a different portion of the connector 500 to lock or secure the connector 500, and thus, the set connector assembly 502, to the housing 220.

Figure 15:
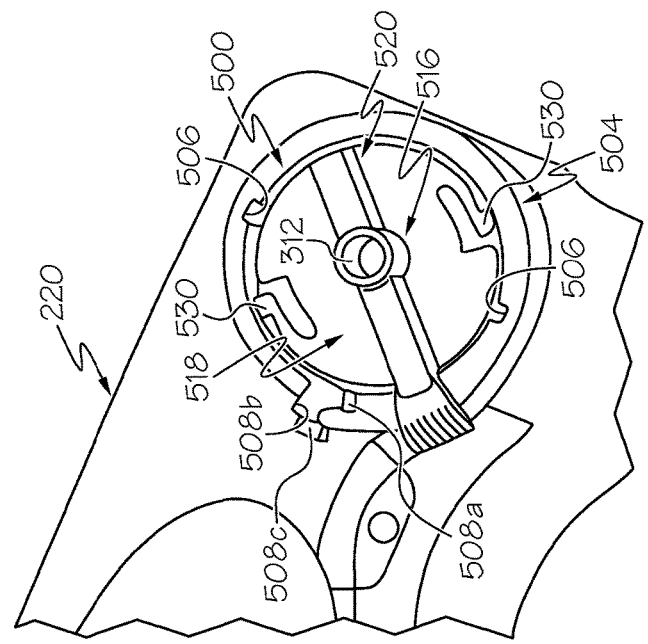
FIG. 15 is a top perspective view of a portion of the fluid infusion device of FIG. 2, with the connector of the set connector assembly of FIG. 14 shown in a second, unlocked position relative to the housing of the fluid infusion device.

The lock 508 is defined in the retaining ring 504. With reference to FIG. 15, the connector 500 is illustrated in a second, unlocked position without the tube 210 for clarity. The lock 508 includes a ramp surface 508a, a wall 508b and a pocket 508c. The ramp surface 508a is defined along a first end of the lock 508, and has a decreasing slope towards the wall 508b. The decreasing slope assists in coupling the set connector assembly 502 to the housing 220. The wall 508b is substantially opposite the ramp surface 508a, and prevents or inhibits the further rotation of the connector 500 relative to the housing 220. The pocket 508c is defined at an end of the ramp surface 508a, between the ramp surface 508a and the wall 508b. The pocket 508c has substantially planar walls, and the pocket 508c is substantially U-shaped to receive a portion of the set connector assembly 502. While the retaining ring 504 is illustrated herein as comprising the lock 508, it will be understood that the housing 220 can include the lock 508, if desired.

The set connector assembly 502 provides a fluid flow path from the fluid reservoir 254 to the user or patient. As the set connector assembly 502 can be similar to the set connector assembly 402 discussed with regard to FIGS. 9-13, the same reference numerals will be used to denote the same or similar components. In one example, the set connector assembly 502 includes the connector 500, the hollow instrument or needle 272 (not shown) and the tube 210. The connector 500 couples the needle 272 and the tube 210 to the fluid reservoir 254, and locks into place once coupled to the fluid reservoir 254 to maintain the fluid flow path between the fluid reservoir 254 and the infusion unit 212 (FIG. 2). The needle 272 defines a flow path for the fluid F out of the fluid reservoir 254, through the connector 500 and into the tube 210.

The set connector assembly 502 (with the fluid reservoir 254 coupled thereto) is coupled to the housing 220 of the fluid infusion device 202 to seal and secure the fluid reservoir 254 inside the housing 220. Thereafter, actuation of the fluid infusion device 202 causes the medication fluid to be expelled from the fluid reservoir 254, through the infusion set component 204, and into the body of the patient via the infusion unit 212 at the distal end of the tube 210. Accordingly, when the set connector assembly 502 is installed as depicted in FIG. 14, the tube 210 extends from the fluid infusion device 202 to the infusion unit 212 (FIG. 2), which in turn provides a fluid pathway to the body of the patient. For this embodiment, the set connector assembly 502 is realized as a removable reservoir cap (or fitting) that is suitably sized and configured to accommodate replacement of fluid reservoirs (which are typically disposable) as needed.

The connector 500 is movably coupled to the housing 220 and retains the fluid reservoir 254 (not shown) within the housing 220. Generally, the connector 500 is composed of a polymeric material, such as a polycarbonate material, and comprises a one-piece monolithic component; however, the connector 500 can be composed of any suitable material and can be assembled from multiple components. In the example of a monolithic polymeric component, the connector 500 can be formed through injection molding, or 3D printing, for example. The connector 500 has a body 510, which defines a graspable portion 512 and a coupling portion 514. The graspable portion 512 is movable relative to the body 510 to move the connector 500 between a first, locked position and a second, unlocked position relative to the housing 220.

The graspable portion 512 includes a hub 516, a first, locking arm 518 and a second arm 520. The hub 516 is coupled to the coupling portion 514. The hub 516 defines the bore 312, which receives the needle 272 (FIG. 3) and the tube 210. The bore 312 is generally defined along the longitudinal axis L of the connector 500.

Figure 16:
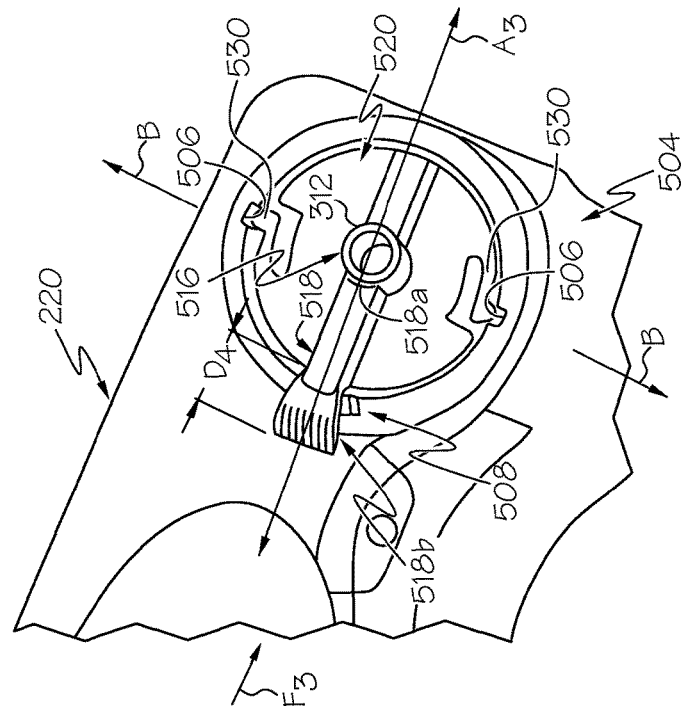
FIG. 16 is a top perspective view of a portion of the fluid infusion device of FIG. 2, with the connector of the set connector assembly of FIG. 14 shown in the first, locked position relative to the housing of the fluid infusion device.

With reference to FIG. 16, the graspable portion 512 is generally symmetric relative to an axis A3. The locking arm 518 is coupled to the hub 516 so as to be substantially opposite the second arm 520. The locking arm 518 extends outwardly from the hub 516, and includes a first end 518a and a second end 518b. Generally, only the first end 518a is coupled to the hub 516 to enable the second end 518b of the locking arm 518 to move or deflect relative to the hub 516. The locking arm 518 generally extends a distance D4 beyond a perimeter of the connector 500 to provide a biasing force (via the compression of the locking arm 518) to lock the locking arm 518 into the lock 508. Similarly, the biasing force created by the locking arm 518 also resists the rotation of the locking arm 518 out of the pocket 508c of the lock 508.

With reference to FIG. 14, the second end 518b of the locking arm 518 cooperates with the lock 508 to lock the connector 500, and thus, the set connector assembly 502 to the housing 220. In one example, the second end 518b includes a locking tab 524 and the graspable surface 436. The locking tab 524 extends from the second end 518b to be received with in the pocket 412 defined by the lock 406. The locking tab 524 is generally rectangular, with a plurality of planar sides, which cooperate with the planar walls of the pocket 508c to prevent or inhibit the rotation of the connector 500 relative to the housing 220, thereby locking the set connector assembly 502 to the housing 220. A relief 524a may be defined adjacent to the locking tab 524 to facilitate the disengagement of the locking tab 524 with the pocket 508c by providing increased flexibility through the removal of material near the locking tab 524. The graspable surface 436 provides a roughened surface to aid a user in the movement of the connector 500 between the first, locked position and the second, unlocked position.

The second arm 520 is spaced apart from the locking arm 518 about the perimeter of the hub 516. The second arm 520 includes a third end 520a and a fourth end 520b. The third end 520a couples the second arm 520 to the hub 516. The second arm 520 cooperates with the locking arm 518 to provide a graspable surface for the user to move the connector 500 between the first, locked position and the second, unlocked position.

The coupling portion 514 extends along the longitudinal axis L, and is substantially cylindrical. As the coupling portion 514 is substantially the same as the coupling portion 302, the coupling portion 514 will not be discussed in great detail herein. Briefly, however, the coupling portion 514 includes the threads 276 (not shown), which are positioned about a circumference of the coupling portion 514. The coupling portion 514 has a first end 514a coupled to the graspable portion 512, and an opposite, second end (not shown). The first end 514a is generally circumferentially closed, to prevent fluids from flowing into and/or out of the housing 220. The second end is generally circumferentially open, to enable the coupling portion 514 to be received about the proximal barrel end 266 of the fluid reservoir 254 (FIG. 3). The coupling portion 514 can also define the one or more recesses 324 about a perimeter or circumference of the coupling portion 514.

In one example, the coupling portion 514 also includes a pair of arms 530. The pair of arms 530 are substantially opposite each other about a perimeter of the coupling portion 514. The arms 530 are generally integrally formed with the coupling portion 514, and include a living hinge that biases the arms 530 in a direction away from the coupling portion 514. Stated another way, with reference to FIG. 16, each of the arms 530 are defined so as to be biased in a direction B. The engagement of the coupling portion 514 with the housing 220 causes the compression of the arms 530 (as shown in FIG. 15), until the arms 530 expand and engage a respective one of the pair of pockets 506 (FIG. 16). Thus, in this example, the arms 530 cooperate with the locking arm 518 to secure or lock the connector 500 to the housing 220. It should be noted, however, that the arms 530 and the pair of pockets 506 are optional, as the locking arm 518 can be used solely to secure or lock the connector 500 to the housing 220.

With the housing 220 assembled, a full fluid reservoir 254 is coupled to the set connector assembly 502. With the needle 272 and the tube 210 (FIG. 3) coupled to the connector 500, the fluid reservoir 254 is coupled to the coupling portion 514 by a bayonet style connection (i.e. push in and twist the connector 500 to couple the fluid reservoir 254 to the connector 500), however, any suitable technique can be employed to couple the fluid reservoir 254 to the connector 500. Generally, the axial insertion of the full fluid reservoir 254 into the connector 500 causes the needle 272 to pierce the septum 268, thereby defining a fluid flow path for the fluid F out of the fluid reservoir 254 (FIG. 3). The full fluid reservoir 254 is rotated relative to the connector 500 to couple the full fluid reservoir 254 to the coupling portion 514. With the fluid reservoir 254 coupled to the set connector assembly 502, the fluid reservoir 254 is inserted into the housing 220 such that the stopper 262 is adjacent to the projection 250 of the slide 238 (FIG. 3). The set connector assembly 502 is then coupled to the housing 220. In one example, the coupling portion 514 is inserted into the housing 220 such that the threads 276 engage the threads 274a (FIG. 3). The connector 500 is rotated, via the graspable portion 512, thereby compressing the arms 530, as shown in FIG. 15. The connector 500 is rotated until the locking tab 524 engages the pocket 508c of the lock 508 and the arms 530 engage the pair of pockets 506. The engagement of the locking tab 524 with the pocket 508c of the lock 508 and the engagement of the arms 530 with the pair of pockets 506 can provide tactile and audible feedback to the user that the connector 500 is locked to the housing 220.

With the locking tab 524 engaged with the pocket 508c, the connector 500, and thus, the set connector assembly 502, is secured or locked to the housing 220. With the set connector assembly 502 coupled to the fluid reservoir 254, one or more control signals from the control module 226 can drive the motor 232, thereby rotating the drive screw 236, which results in the linear translation of the slide 238. The advancement of the slide 238 into the fluid reservoir 254 moves the stopper 262, causing the fluid F to flow from the fluid reservoir 254 through the fluid flow path defined by the set connector assembly 502.

With reference to FIG. 15, the connector 500 is shown in the first, locked position, secured or locked to the housing 220. Thus, during movement of the user, the set connector assembly 502 is prevented or inhibited from inadvertently moving or rotating, thereby ensuring an uninterrupted fluid flow path from the fluid reservoir 254 through the tube 210.

In order to remove the set connector assembly 502, for example, to replace an empty fluid reservoir 254, with reference to FIG. 16, a force F3 can be applied to the locking arm 518, while rotating the graspable portion 512 to move the locking tab 524 out of the pocket 508c of the lock 508 and the arms 530 out of engagement with the pair of pockets 506. Once the locking tab 524 is released from the pocket 508c, the connector 500 can be rotated, via the graspable portion 512, to remove the connector 500 from the housing 220 or move the connector 500 to the second, unlocked position.

Figure 17:
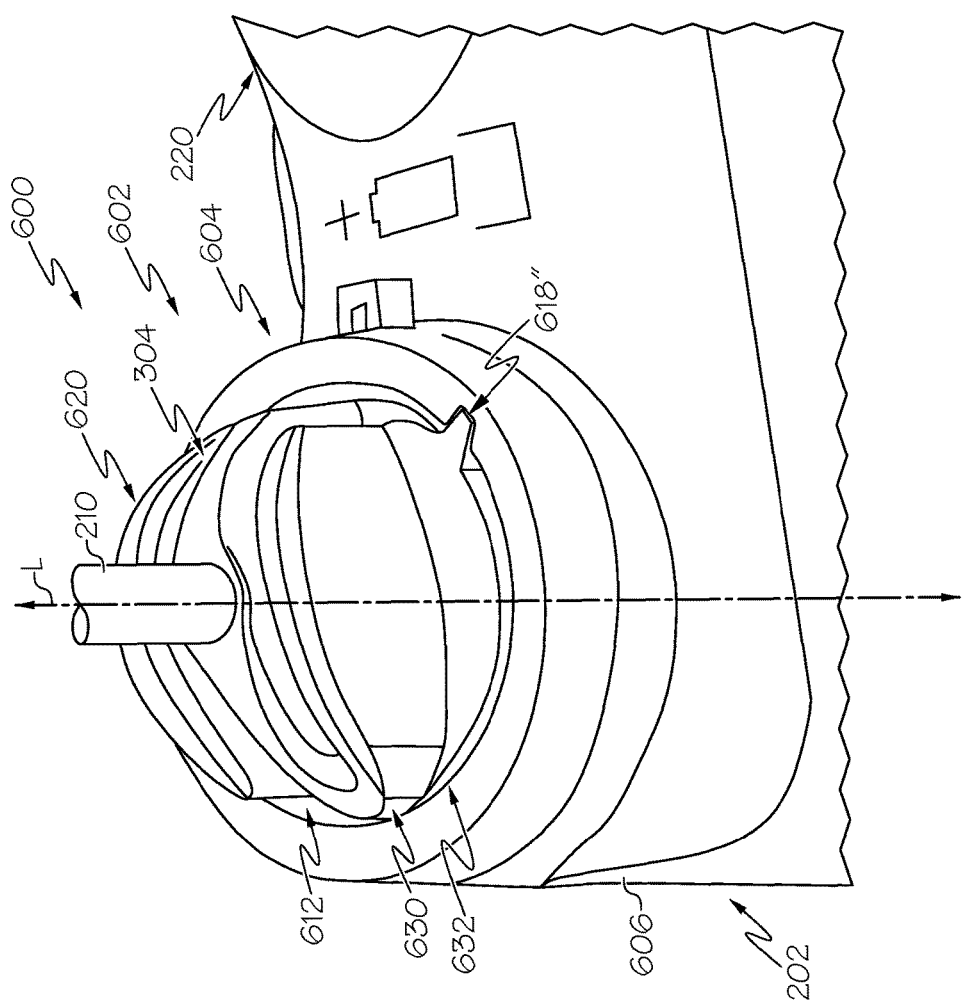
FIG. 17 is a side perspective view of a portion of the fluid infusion device of FIG. 2, with a connector of an exemplary set connector assembly in a first, locked position relative to the housing of the fluid infusion device in accordance with the various teachings of the present disclosure.

With reference to FIG. 17, a connector 600 for use with a set connector assembly 602 is shown. The set connector assembly 602 can be used with the infusion set component 204 and the fluid infusion device 202 of FIG. 2, and can be used as an alternative to the set connector assembly 214. In this example, the fluid infusion device 202 includes a retaining ring 604 which is similar to the retaining ring 258. Stated another way, the set connector assembly 602 necessitates the retaining ring 604 to secure or lock the set connector assembly 602 to the housing 220 of the fluid infusion device 202. The remainder of the fluid infusion device 202 remains unchanged from that of FIGS. 1-8, and thus, only the differences in the fluid infusion device 202 associated with the use of the set connector assembly 602 will be discussed in detail herein. In this example, the retaining ring 604 is coupled to the housing 220, via ultrasonic welding, for example, to retain the sealing member 256 within the housing 220 (FIG. 3).

The retaining ring 604 cooperates with the set connector assembly 602 to aid in coupling the connector 600 to the fluid reservoir 254, as will be discussed in greater detail herein. The retaining ring 604 is coupled to a portion of the housing 220 and substantially surrounds the opening defined in the housing 220 that receives the fluid reservoir 254. The retaining ring 604 is coupled to the housing 220 about the opening such that the sealing member 256 (FIG. 3) is disposed between the housing 220 and the retaining ring 604. In one example, the retaining ring 604 is substantially annular; however, the retaining ring 604 can have any suitable shape that corresponds to the shape of the portion of the housing 220 that receives the fluid reservoir 254.

The retaining ring 604 includes one or more locks 606, which cooperate with the set connector assembly 602 to lock the set connector assembly 602 to the housing 220. In this example, with reference to FIG. 18, the retaining ring 604 comprises two locks 606 that are positioned substantially opposite each other about a circumference of the retaining ring 604. It should be noted, however, that any number of locks 606 can be employed and the locks 606 can be positioned at any desired location about the circumference of the retaining ring 604. In one example, the locks 606 are substantially triangular pockets, and are sized to receive a portion of the connector 600. In this example, the locks 606 include a plurality of planar wall surfaces 606a, 606b and 606c, which cooperate to define the locks 606. Generally, the locks 606 include three planar wall surfaces 606a, 606b, 606c, which are connected together to define the substantially triangular shape of the locks 606. It should be noted, however, that the locks 606 can have any desired shape, and moreover, the locks 606 need not have the same shape. Further, the locks 606 can include one or more ramp surfaces, if desired. In this example, the planar wall surfaces 606a act as a stop for the connector 600, while the planar wall surface 606c provides clearance for the connector 600 within the locks 606. Generally, the planar wall surface 606c has a length L6 that extends for a distance that is different than, and generally less than, a length L7 of the planar wall surface 606a to facilitate the removal of the connector 600 from the locks 606.

With reference to FIG. 19, the connector 600 of the set connector assembly 602 is shown in greater detail. In FIG. 19, the connector 600 is illustrated without the needle 272 and the tube 210 for clarity. The connector 600 is removably coupled to the housing 220 and retains the fluid reservoir 254 (FIG. 3) within the housing 220. Generally, the connector 600 is composed of a polymeric material, such as a polycarbonate material, and comprises a one-piece monolithic component; however, the connector 600 can be composed of any suitable material and can be assembled from multiple components. In the example of a monolithic polymeric component, the connector 600 can be formed through injection molding, or 3D printing, for example. The connector 600 has a body 610, which defines a graspable portion 612 and the coupling portion 302. The body 610 extends along the longitudinal axis L. The graspable portion 612 is movable relative to the body 610 to move the connector 600 between a first, locked position and a second, unlocked position relative to the housing 220.

The graspable portion 612 includes the main branch 304, a first wing 614 and a second wing 616. The main branch 304 extends from the coupling portion 302 and couples the graspable portion 612 to the coupling portion 302. One or more of the first wing 614 and the second wing 616 define a locking tab 618. In this example, the first wing 614 defines a locking tab 618', and the second wing 616 defines a locking tab 618". The locking tabs 618', 618" are substantially similar on both the first wing 614 and the second wing 616; however, it should be understood that the locking tabs 618', 618" need not be substantially identical. The graspable portion 612 is generally mirror symmetric about an axis A4.

The main branch 304 generally extends away from the coupling portion 302 to define the gap 314 between the first wing 614 and the second wing 616. The gap 314 enables the first wing 614 and the second wing 616 to move relative to the main branch 304, thereby engaging or disengaging the locking tabs 618', 618", as will be discussed in greater detail herein. Stated another way, the main branch 304 couples the graspable portion 612 to the coupling portion 302 such that the gap 314 is defined between the first wing 614, the second wing 616 and the coupling portion 302. In other words, the first wing 614 and the second wing 616 are not coupled to the coupling portion 302, but rather, the first wing 614 and the second wing 616 are movable relative to the coupling portion 302 and are each coupled solely to the main branch 304.

Figure 18:
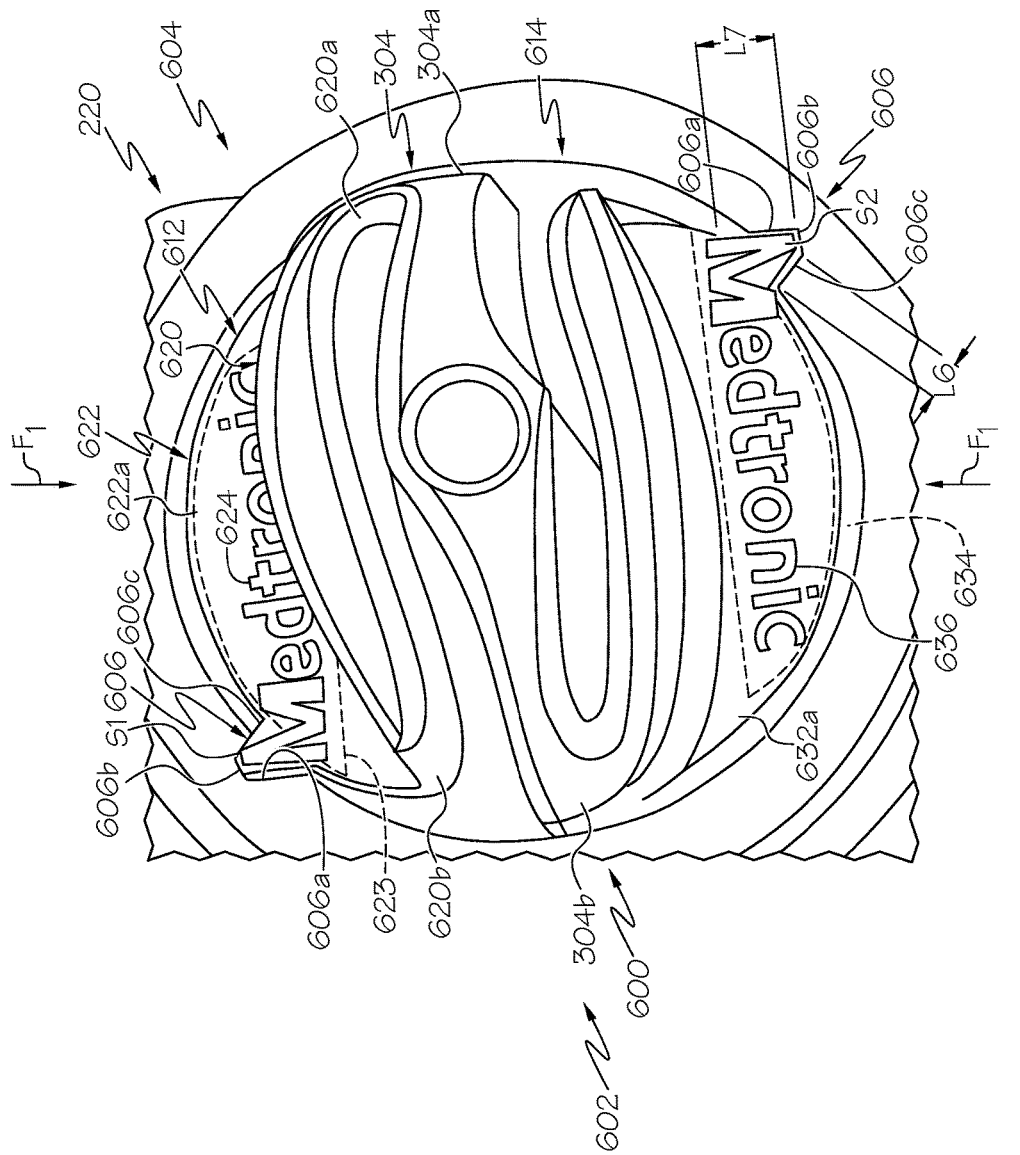
FIG. 18 is a top view of the connector of FIG. 17, which includes exemplary markings on a surface of the connector.

The main branch 304 includes the first end 304a and the opposite, second end 304b. The first wing 614 is coupled to the first end 304a, and the second wing 616 is coupled to the second end 304b. Generally, the first wing 614 is coupled to the first end 304a such that the first wing 614 extends from the first end 304a in a first direction towards the second end 304b of the main branch 304, and the second wing 616 is coupled to the second end 304b such that the second wing 616 extends from the second end 304b in a second direction towards the first end 304a. The second direction is different than the first direction, and in this example, is substantially opposite the first direction. The first wing 614 includes a first arm 620 and a first flange 622. The first arm 620 is coupled to the first end 304a, and extends upwardly from the first flange 622 so as to be adjacent to the top surface 304c of the main branch 304. The first arm 620 is substantially arcuate, and includes a first arm end 620a and a second arm end 620b. The first arm end 620a is coupled to the first end 304a at a living hinge. The second arm end 620b extends from the first arm end 620a, in a direction toward the second end 304b of the main branch 304. Generally, the second arm end 620b does not extend to the second end 304b, but rather, extends for a length that is different than, and for example, less than, the length L2 of the main branch 304. The first flange 622 is coupled to the first arm 620 and extends along the first arm 620 from the first arm end 620a to the second arm end 620b, as illustrated in FIG. 18. As shown in FIG. 19, the first flange 622 is adjacent to the gap 314. Generally, the first flange 622 extends outwardly from the first arm 620 along an axis, which is transverse to the longitudinal axis L, and in one example, is substantially perpendicular to the longitudinal axis L. The first flange 622 is generally semi-circular, and defines the locking tab 618'.

In one example, with reference to FIG. 18, the first flange 622 also defines an area 623 on a surface 622a of the first flange 622. The area 623 generally receives a marking 624. The marking 624 comprises one or more letters, symbols or graphical icons, as illustrated in FIG. 18. In various examples, the marking 624 is a logo or trademark, and in one example, the marking 624 on the area 623 comprises the text: "MEDTRONIC" ®. It should be noted, however, that the area 623 can also receive a graphical symbol and text, such as a letter, word or phrase with a graphical icon. Generally, the marking 624 is embossed onto the area 623, however, the marking 624 can be integrally formed with the formation of the connector 600 (i.e. printed or molded), applied to the area 623 via a label adhered to the area 623 with an adhesive, etc. In this example, the marking 624 is defined on at least a portion, if not an entirety, of a surface S1 of the locking tab 618'. Thus, at least a portion of the surface 622a of the first flange 622, including the locking tab 618', is labeled with the marking 624. It should be noted that an entirety of the surface 622a and the surface Si of the locking tab 618' can include the marking 624, if desired.

The locking tab 618' extends outwardly from the first flange 622 so as to extend beyond a perimeter of the body 610 of the connector 600. The locking tab 618' is defined on the first flange 622 so as to be adjacent to the second arm end 620b. Stated another way, the locking tab 618' is defined at a second end of the first flange 622, with the second end of the first flange 622 coupled to the second arm end 620b. With reference to FIG. 19, the locking tab 618' has a first planar surface 625, a second planar surface 626 and a third planar surface 628. The planar surfaces 625, 626, 628 cooperate to define a substantially triangular shape for the locking tab 618'. The first planar surface 625 has a length L8, which is different than, and generally greater than a length L9 of the third planar surface 628. The first planar surface 625 cooperates with the planar wall surfaces 606a of a respective one of the locks 606 to prevent the further rotation of the connector 600 relative to the housing 220. The third planar surface 628 cooperates with the planar wall surfaces 606c of the respective one of the locks 606 to assist in guiding the locking tab 618' out of engagement with the respective one of the locks 606 when the connector 600 is moved from the first, locked position to the second, unlocked position, as will be discussed further herein.

The second wing 616 includes a second arm 630 and a second flange 632. The second arm 630 is coupled to the second end 304b, and extends upwardly from the second flange 632 so as to be adjacent to the top surface 304c of the main branch 304. The second arm 630 is substantially arcuate, and includes a third arm end 630a and a fourth arm end 630b. The third arm end 630a is coupled to the second end 304b at a living hinge. The fourth arm end 630b extends from the third arm end 630a, in a direction toward the first end 304a of the main branch 304. Generally, the fourth arm end 630b does not extend to the first end 304a, but rather, extends for a length that is different than, and for example, less than, the length L2 of the main branch 304. The second flange 632 is coupled to the second arm 630 and extends along the second arm 630 from the third arm end 630a to the fourth arm end 630b. As illustrated in FIG. 19, the second flange 632 is adjacent to the gap 314. Generally, the second flange 632 extends outwardly from the second arm 630 along an axis, which is transverse to the longitudinal axis L, and in one example, is substantially perpendicular to the longitudinal axis L. The second flange 632 is generally semi-circular, and defines the locking tab 618".

In one example, with reference to FIG. 18, the second flange 632 defines a second area 634 on a surface 632a of the second flange 632. The second area 634 generally receives a second marking 636. The marking 634 comprises one or more letters, symbols or graphical icons, as illustrated in FIG. 18. In various examples, the second marking 636 is a logo or trademark, and in one example, the second marking 636 on the second area 634 comprises the text: "MEDTRONIC" ®. It should be noted, however, that the second area 634 can also receive a graphical symbol and text, such as a letter, word or phrase with a graphical icon. Generally, the second marking 636 is embossed onto the second area 634, however, the second marking 636 can be integrally formed with the formation of the connector 600 (i.e. printed or molded), applied to the second area 634 via a label adhered to the second area 634 with an adhesive, etc. In this example, the second marking 636 is defined on at least a portion, if not an entirety, of a surface S2 of the locking tab 618". Thus, at least a portion of the surface 632a of the second flange 632, including the locking tab 618", is labeled with the second marking 636. It should be noted that an entirety of the surface 632a and the surface S2 of the locking tab 618" can include the second marking 636, if desired.

It should be noted that while the marking 624 and the second marking 636 are illustrated herein as comprising the same text, the marking 624 and the second marking 636 need not include the same letters and/or symbols. Moreover, one or both of the marking 624 and the second marking 636 can also include a color that is different than a color of the body 610, to enable the marking 624 and the second marking 636 to visually stand out or be visually distinct from the body 610 of the connector 600. In this example, the marking 624 and/or the second marking 636 can be painted. Alternatively, the marking 624 and/or the second marking 636 can have a different texture than the body 610 to provide a tactile indicator of the marking 624 and/or the second marking 636. Further, although the marking 624 and the second marking 636 are illustrated herein as comprising an embossing having recesses or depressions in the area 623 and second area 634, one or both of the marking 624 and the second marking 636 can be raised or extend upwardly from the area 623 and the second area 634. In addition, one or more of the locking tabs 618', 618" can have a shape that corresponds to the marking 624 and/or the second marking 636, and thus, the triangular shape of the locking tabs 618', 618" that correspond to a portion of the "M" of the marking 624 and/or the second marking 636 is merely an example.

With reference to FIG. 19, the locking tab 618" extends outwardly from the second flange 632 so as to extend beyond a perimeter of the body 610 of the connector 600. The locking tab 618" is defined on the second flange 632 so as to be adjacent to the fourth arm end 630b. Stated another way, the locking tab 618" is defined at a second end of the second flange 632, with the second end of the second flange 632 coupled to the fourth arm end 630b. The locking tab 618" has the first planar surface 625, the second planar surface 626 and the third planar surface 628. The first planar surface 625 cooperates with the planar wall surfaces 606a of a respective one of the locks 606 to prevent the further rotation of the connector 600 relative to the housing 220. The third planar surface 628 cooperates with the planar wall surfaces 606c of the respective one of the locks 606 to assist in guiding the locking tab 618" out of engagement with the respective one of the locks 606 when the connector 600 is moved from the first, locked position to the second, unlocked position, as will be discussed further herein.

With the housing 220 assembled, a full fluid reservoir 254 (FIG. 3) is coupled to the set connector assembly 602. With the needle 272 and the tube 210 coupled to the connector 600, the fluid reservoir 254 is coupled to the coupling portion 302 by a bayonet style connection (i.e. push in and twist the connector 600 to couple the fluid reservoir 254 to the connector 600), however, any suitable technique can be employed to couple the fluid reservoir 254 to the connector 600. Generally, with the needle 272 and the tube 210 coupled to the connector 600, the axial insertion of the full fluid reservoir 254 into the connector 600 causes the needle 272 to pierce the septum 268, thereby defining a fluid flow path for the fluid F out of the fluid reservoir 254 (FIG. 3). The full fluid reservoir 254 is then rotated relative to the connector 600 to couple the full fluid reservoir 254 to the coupling portion 302. With the fluid reservoir 254 coupled to the set connector assembly 602, the fluid reservoir 254 is inserted into the housing 220 such that the stopper 262 is adjacent to the projection 250 of the slide 238 (FIG. 3). In one example, the coupling portion 302 is inserted into the housing 220 such that the threads 276 engage the threads 274a (FIG. 3). The connector 600 is rotated, via the graspable portion 612, until the locking tabs 618', 618" engage with the respective locks 606. The engagement of the locking tabs 618', 618" with the respective locks 606 can provide tactile and audible feedback to the user that the connector 600 is locked to the housing 220.

With the locking tabs 618', 618" engaged with the respective locks 606, the connector 600, and thus, the set connector assembly 602, is secured or locked to the housing 220. With the set connector assembly 602 coupled to the fluid reservoir 254, one or more control signals from the control module 226 can drive the motor 232, thereby rotating the drive screw 236, which results in the linear translation of the slide 238 (FIG. 3). The advancement of the slide 238 into the fluid reservoir 254 moves the stopper 262, causing the fluid F to flow from the fluid reservoir 254 through the fluid flow path defined by the set connector assembly 602.

With reference to FIG. 17, the connector 600 is shown in the first, locked position, secured or locked to the housing 220. Thus, during movement of the user, the set connector assembly 602 is prevented or inhibited from inadvertently moving or rotating, thereby ensuring an uninterrupted fluid flow path from the fluid reservoir 254 through the tube 210. Stated another way, the connector 600 reduces and eliminates the need for an activity guard that locks over a portion of the housing 220 containing the fluid reservoir 254. In this regard, the locking tabs 618', 618" securely couple and lock the fluid reservoir 254 to and within the housing 220, thereby reducing and substantially eliminating the need for an additional guard against the inadvertent removal of the fluid reservoir 254.

In order to remove the set connector assembly 602, for example, to replace an empty fluid reservoir 254, with reference to FIG. 18, the force F1 can be applied to the first wing 614 and the second wing 616 to move the connector 600 from the first, locked position to the second, unlocked position. The application of the force F1 causes the first wing 614 and the second wing 616 to deflect inward, toward the main branch 304. The inward deflection of the first wing 614 and the second wing 616 causes the respective locking tab 618', 618" to move inward, thereby removing the locking tabs 618', 618" from the locks 606. With the locking tabs 618', 618" removed from the locks 606, the connector 600 can be rotated, for example, in a counterclockwise direction, and removed from the housing 220 or moved to the second, unlocked position.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A set connector assembly for a fluid infusion device, comprising:
a connector having a body, the body defining a graspable portion and a coupling portion, the coupling portion to be received within a portion of the fluid infusion device, and the graspable portion includes a hub coupled to the coupling portion and a locking arm having a first end coupled to the hub and a second end that has a locking tab to lock the connector to the fluid infusion device, the hub defines a bore that extends along a longitudinal axis of the connector, the first end of the locking arm coupled to the hub such that a space is defined between the locking tab and the hub to receive a portion of the fluid infusion device, the locking arm movable relative to the coupling portion to move the connector between a first, locked position and a second, unlocked position relative to the fluid infusion device and the locking arm extends a distance beyond a perimeter of the coupling portion to provide a force to bias the locking arm into the lock.

2. The set connector assembly of claim 1, wherein the graspable portion includes a second arm opposite the locking arm.

3. The set connector assembly of claim 1, wherein the graspable portion comprises at least one wing coupled adjacent to the locking arm.

4. The set connector assembly of claim 1, wherein the bore is to receive a needle and a tube, to define a fluid flow path out of the fluid infusion device.

5. The set connector assembly of claim 1, wherein the graspable portion includes a first wing and a second wing coupled to the hub such that the first wing is substantially opposite the second wing about the hub.

6. The set connector assembly of claim 5, wherein the locking arm is coupled to the hub between the first wing and the second wing.

7. The set connector assembly of claim 5, wherein at least one of the first wing and the second wing includes an undulating surface at an end.

8. A fluid infusion device, comprising:
a housing that includes a lock and defines an opening that receives a removable fluid reservoir, the lock spaced apart from the opening; and
a set connector assembly removably coupled to the housing to define a fluid flow path from the removable fluid reservoir of the fluid infusion device, the set connector assembly including a connector having a body, the body defining a graspable portion and a coupling portion, the coupling portion receivable within the opening of the housing and coupled to the removable fluid reservoir, and the graspable portion includes a hub coupled to the coupling portion and a locking arm having a first end coupled to the hub and a second end that has a locking tab that engages the lock, the hub defines a bore that extends along a longitudinal axis of the connector for defining the fluid flow path, the locking arm movable relative to the coupling portion to move the connector between a first, locked position and a second, unlocked position relative to the housing and the locking arm extends a distance beyond a perimeter of the coupling portion to provide a force to bias the locking arm into the lock.

9. The fluid infusion device of claim 8, wherein the lock is coupled to a surface of the housing so as to be adjacent to a fluid reservoir system associated with the fluid infusion device.

10. The fluid infusion device of claim 8, wherein the graspable portion includes a second arm opposite the locking arm.

11. The fluid infusion device of claim 8, wherein the graspable portion comprises at least one wing coupled adjacent to the locking arm.

12. The fluid infusion device of claim 8, wherein the graspable portion includes a first wing and a second wing coupled to the hub such that the first wing is substantially opposite the second wing about the hub and the locking arm is coupled to the hub between the first wing and the second wing.

13. The fluid infusion device of claim 8, wherein the housing includes a retaining ring coupled to the housing that defines the lock, and the lock includes a pocket that receives the locking tab.

14. The fluid infusion device of claim 9, wherein the bore is to receive a needle and a tube, the needle receivable within a fluid reservoir of the fluid reservoir system to define the fluid flow path out of the fluid infusion device.

15. A fluid infusion device, comprising:
a removable fluid reservoir;
a housing defining an opening that receives the removable fluid reservoir, the housing including a lock spaced apart from the opening; and
a set connector assembly removably coupled to the housing to define a fluid flow path from the removable fluid reservoir, the set connector assembly including a connector having a body, the body defining a graspable portion and a coupling portion, the coupling portion receivable within the housing and positionable about the removable fluid reservoir, the graspable portion having a hub and a locking arm that has a first end coupled to the hub and a second end that defines a locking tab that engages the lock, the hub coupled to the coupling portion and defining a bore that extends along a longitudinal axis of the connector to define the fluid flow path, the first end of the locking arm coupled to the hub such that a space is defined between the locking tab and the hub to receive a portion of the housing and the locking arm is movable relative to the coupling portion to move the connector between a first, locked position and a second, unlocked position relative to the housing and the locking arm extends a distance beyond a perimeter of the coupling portion to provide a force to bias the locking arm into the lock.

16. The fluid infusion device of claim 15, wherein the housing includes a retaining ring coupled to the housing that defines the lock, and the lock includes a pocket that receives the locking tab.

17. The fluid infusion device of claim 15, wherein the graspable portion includes a first wing and a second wing coupled to the hub such that the first wing is substantially opposite the second wing about the hub and the locking arm is coupled to the hub between the first wing and the second wing.

* * * * *